US009145572B2

(12) United States Patent
Nakamura

(10) Patent No.: US 9,145,572 B2
(45) Date of Patent: *Sep. 29, 2015

(54) OBSERVATION SYSTEM, RECORDING MEDIUM, AND CONTROL METHOD OF OBSERVATION SYSTEM

(71) Applicant: Panasonic Healthcare Holdings Co., Ltd., Minato-ku, Tokyo (JP)

(72) Inventor: Akira Nakamura, Hirakata (JP)

(73) Assignee: PANASONIC HEALTHCARE HOLDINGS CO., LTD. (JP)

( * ) Notice: Subject to any disclaimer, the term of this patent is extended or adjusted under 35 U.S.C. 154(b) by 144 days.

This patent is subject to a terminal disclaimer.

(21) Appl. No.: 13/946,421

(22) Filed: Jul. 19, 2013

(65) Prior Publication Data

US 2013/0309710 A1 Nov. 21, 2013

Related U.S. Application Data

(63) Continuation of application No. PCT/JP2012/080381, filed on Nov. 22, 2012.

(30) Foreign Application Priority Data

Dec. 22, 2011 (JP) ................................. 2011-281559

(51) Int. Cl.
*G06K 9/00* (2006.01)
*C12Q 1/02* (2006.01)
(Continued)

(52) U.S. Cl.
CPC .................. *C12Q 1/02* (2013.01); *C12M 41/36* (2013.01); *G01N 15/1463* (2013.01); *G01N 2015/1006* (2013.01)

(58) Field of Classification Search
USPC ......... 382/100, 103, 106–107, 128–133, 155, 382/162, 168, 173, 181, 190, 203, 209, 219, 382/224, 232, 254, 274, 276, 286, 291, 305, 382/312; 435/6.1, 4, 7.2; 348/46
See application file for complete search history.

(56) References Cited

U.S. PATENT DOCUMENTS 6,330,349 B1 * 12/2001 Hays et al. ..................... 382/128
8,435,738 B2 * 5/2013 Holmes .......................... 435/6.1
(Continued)

FOREIGN PATENT DOCUMENTS

JP 04326993 A 11/1992
JP 08338705 A 12/1996
(Continued)

*Primary Examiner* — Seyed Azarian
(74) *Attorney, Agent, or Firm* — Cantor Colburn LLP

(57) ABSTRACT

An observation system to observe a sample mass formed of samples gathering in a container containing the samples and a solution, includes: an entire image pickup unit to image the entire container; a sample mass identification unit to identify a sample mass formed in the container, from a macro observation image obtained by imaging the entire container; a magnifying image pickup unit to magnify and image a part of an area in the container including the sample mass identified by the sample mass identification unit; and a history information storage unit to store position information of the sample mass in association with time and date information, wherein the magnifying image pickup unit magnifies and images a part of an area in the container based on the past position information stored in the history information storage unit, while the sample mass identification unit is executing processing of identifying the sample mass.

11 Claims, 13 Drawing Sheets

(51) Int. Cl.
   C12M 1/34  (2006.01)
   G01N 15/14  (2006.01)
   G01N 33/53  (2006.01)
   G01N 15/10  (2006.01)

(56) References Cited

U.S. PATENT DOCUMENTS 8,780,181 B2 * 7/2014 Olesen et al. .................. 348/46

2007/0231785 A1 * 10/2007 Hoyt et al. ..................... 435/4
2008/0279441 A1 * 11/2008 Matsuo et al. ................ 382/133

FOREIGN PATENT DOCUMENTS

| JP | 2005295818 A | 10/2005 |
| JP | 2009198709 A | 9/2009 |
| JP | 2009282198 A | 12/2009 |
| JP | 2010112969 A | 5/2010 |
| JP | 2010527007 A | 8/2010 |

* cited by examiner

OBSERVATION HISTORY TABLE 211

| CONTAINER NO. | COORDINATES OF CELL MASS | DATE | POSITION DETECTION | MAGNIFIED IMAGE PICKUP | DETAIL JUDGEMENT |
|---|---|---|---|---|---|
| 0001 | 345.480 | 2011/10/01 | Y | Y | Y |
| 0001 | 628.918 | 2011/10/01 | Y | Y | N |
| 0001 | 1477.619 | 2011/10/01 | N | Y | N |
| ... | ... | ... | ... | ... | ... |

FIG. 6

OBSERVATION SYSTEM, RECORDING MEDIUM, AND CONTROL METHOD OF OBSERVATION SYSTEM

CROSS-REFERENCE TO RELATED APPLICATIONS

This application is a continuation under 35 U.S.C. §120 of PCT/JP2012/080381, filed Nov. 22, 2012, which is incorporated herein reference and which claimed priority to Japanese Application No. 2011-281559, filed Dec. 22, 2011. The present application likewise claims priority under 35 U.S.C. §119 to Japanese Application No. 2011-281559, filed Dec. 22, 2011, the entire content of which is also incorporated herein by reference.

BACKGROUND OF THE INVENTION

1. Field of the Invention

The present invention relates to an observation system, a recording medium, and a control method of observation system.

2. Description of the Related Art

In culturing cells, if observation can be started concurrently with emergence of a cell mass having a plurality of cells gathering therein and the observation can be conducted sequentially in chronological order, it can be a promising technique to support regenerative medicine, for example. Such observation of cells has been conducted, by using a microscope, for example, when replenishment or replacement of culture fluid in a culture container is required during cell culture, and an image has been picked up as necessary.

However, observation of cells using a microscope requires much expense in time and effort. For example, in order to identify a cell mass having emerged in a container, first, the entire container needs to be observed visually or by using a microscope, and then, a growing state of the individual cell mass needs to be observed under magnification by replacing an objective lens, for example. In micro observation, a narrow field of view causes difficulty in searching a target cell mass, and also causes difficulty in adjusting the cell mass to the field of view. When observing cells, it is preferable to conduct time-lapse observation in which a long-term change is observed from a time of emergence of the cell mass to a time of completion of growth thereof for every predetermined time period. Since the cell mass cannot be observed visually or by using a low-magnification microscope, for example, immediately after seeding of the cell, an observation position needs to be searched and set again several days later.

Further, in observation that is conducted at the time of replenishment or replacement of culture fluid in a culture container usually once in one to three days, it is difficult to conduct observation from a time of emergence of a cell mass, and thus a technique capable of observation of a cell mass from the time of emergence thereof is in high demand. Further, in picking up an image of a cell in each of the cases where the entire container is observed and where a part of the interior of the container is observed under magnification, such a problem that heat generated from illumination and a lens driving system, for example, has effects on growth of the cell arises.

With respect to such observation of cells, a device has been proposed that is configured to save time and effort in switching between the observation of the entire container and the micro observation of a part of the interior of the container, and examples can be found in Japanese Laid-Open Patent Publications 2009-198709 and 2005-295818.

However, it is not easy to manually detect an observation target cell mass in the entire container. Thus, it is preferable that a macro observation image obtained by picking up an image of the entire container is subjected to image processing, thereby extracting the observation target cell mass, and magnifying the portion of the cell mass, as necessary, and imaging it.

However, in that case, image processing for detecting the observation target cell mass from the macro observation image is complicated and requires processing time of several minutes depending on the number of pixels of the macro observation image.

Further, a plurality of observation target cell masses are usually detected in a single container. Thus, a work of individually detecting those cell masses through image processing and picking up an image of each of them needs to be carried out repeatedly, which causes prolonged observation time.

Thus, such a technique is desired that enables an increase in efficiency of the work of detecting a observation target cell mass in the container and magnifying and picking up an image of a portion of each cell mass.

SUMMARY OF THE INVENTION

An observation system according to an aspect of the present invention, which is configured to observe a sample mass formed of samples gathering in a container containing the samples and a solution, the observation system includes: an entire image pickup unit configured to pick up an image of the entire container; a sample mass identification unit configured to identify a sample mass formed in the container, from a macro observation image obtained by picking up an image of the entire container; a magnifying image pickup unit configured to magnify and pick up an image of a part of an area in the container including the sample mass identified by the sample mass identification unit; and a history information storage unit configured to store position information of the sample mass in association with time and date information, the magnifying image pickup unit further configured to magnify and pick up an image of a part of an area in the container based on the past position information stored in the history information storage unit, while the sample mass identification unit is executing processing of identifying the sample mass.

Other features of the present invention will become apparent from descriptions of this specification and of the accompanying drawings.

BRIEF DESCRIPTION OF THE DRAWINGS

For more thorough understanding of the present invention and advantages thereof, the following description should be read in conjunction with the accompanying drawings, in which:

FIG. 6 is a diagram illustrating an observation history table;

DETAILED DESCRIPTION OF THE INVENTION

At least the following details will become apparent from descriptions of this specification and of the accompanying drawings.

Hereinafter, embodiments of the present invention will be described with reference to FIGS. 1 to 13. Note that, for example, a cell in samples such as a cell, a germ, a microorganism will be described as a sample, and a culture fluid will be described as a solution. Further, a cell mass having a plurality of cells gathering therein will be described as a sample mass.

First Embodiment

Entire Configuration

Figure 1:
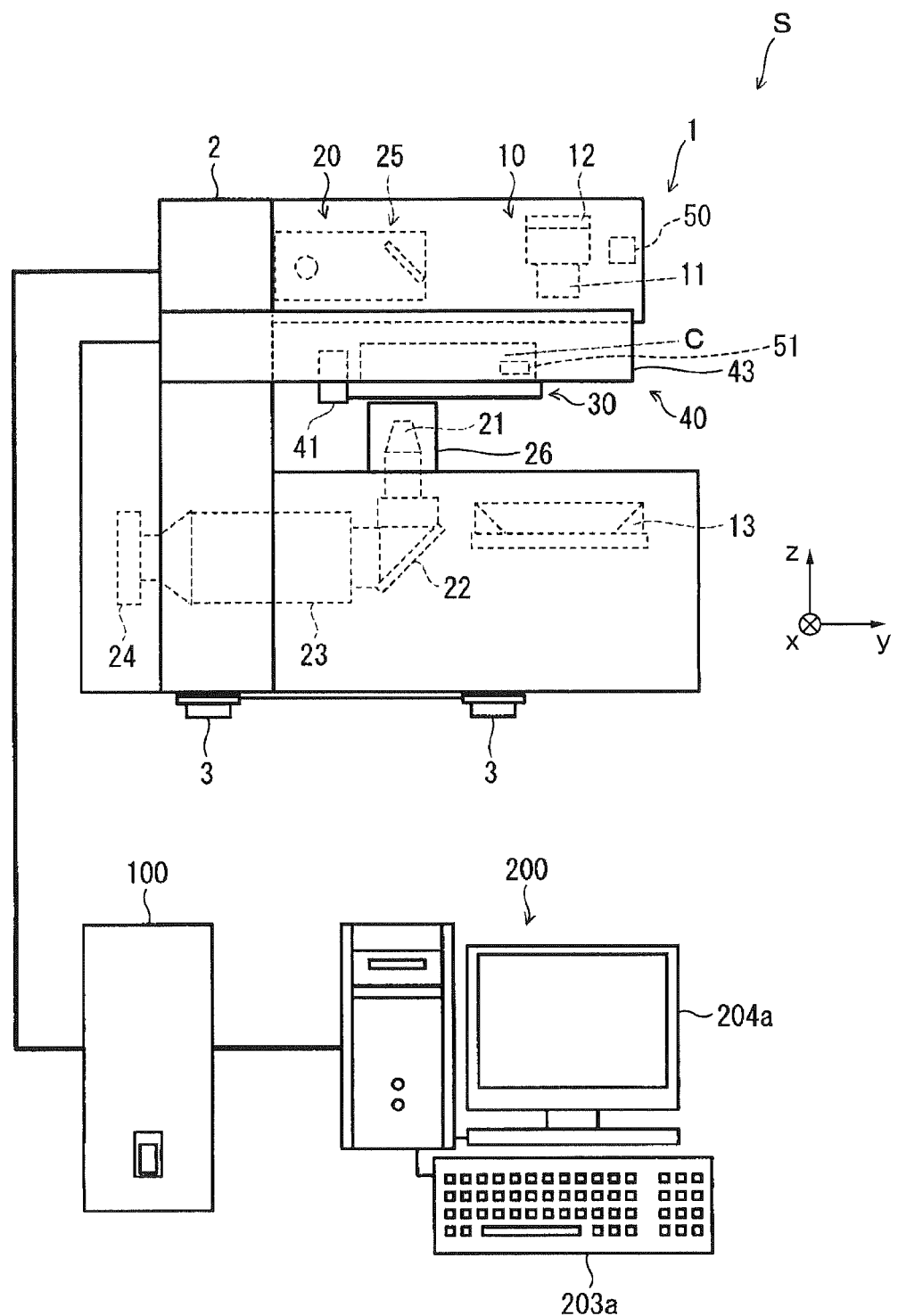
FIG. 1 is a configuration diagram of an observation system.
Figure 2:
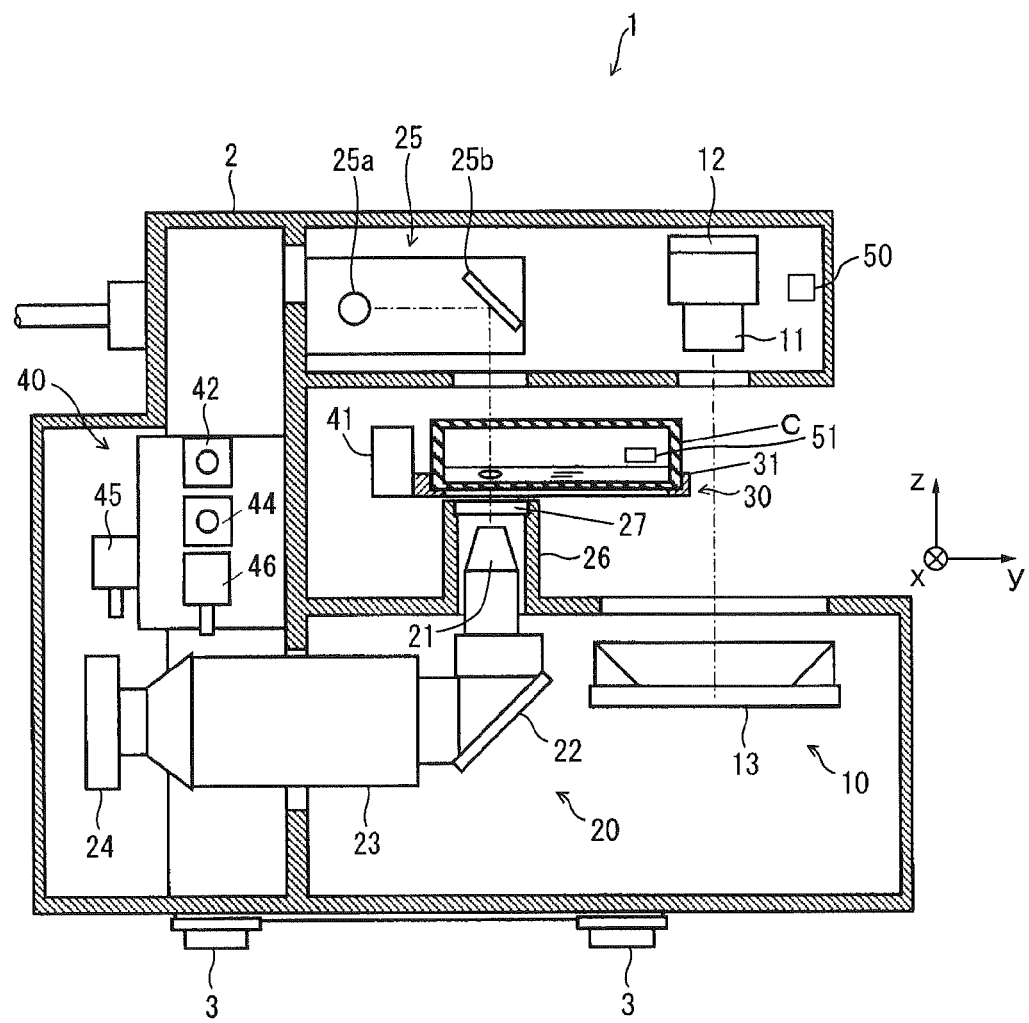
FIG. 2 is a perpendicular sectional side view of an observation apparatus.
Figure 3:
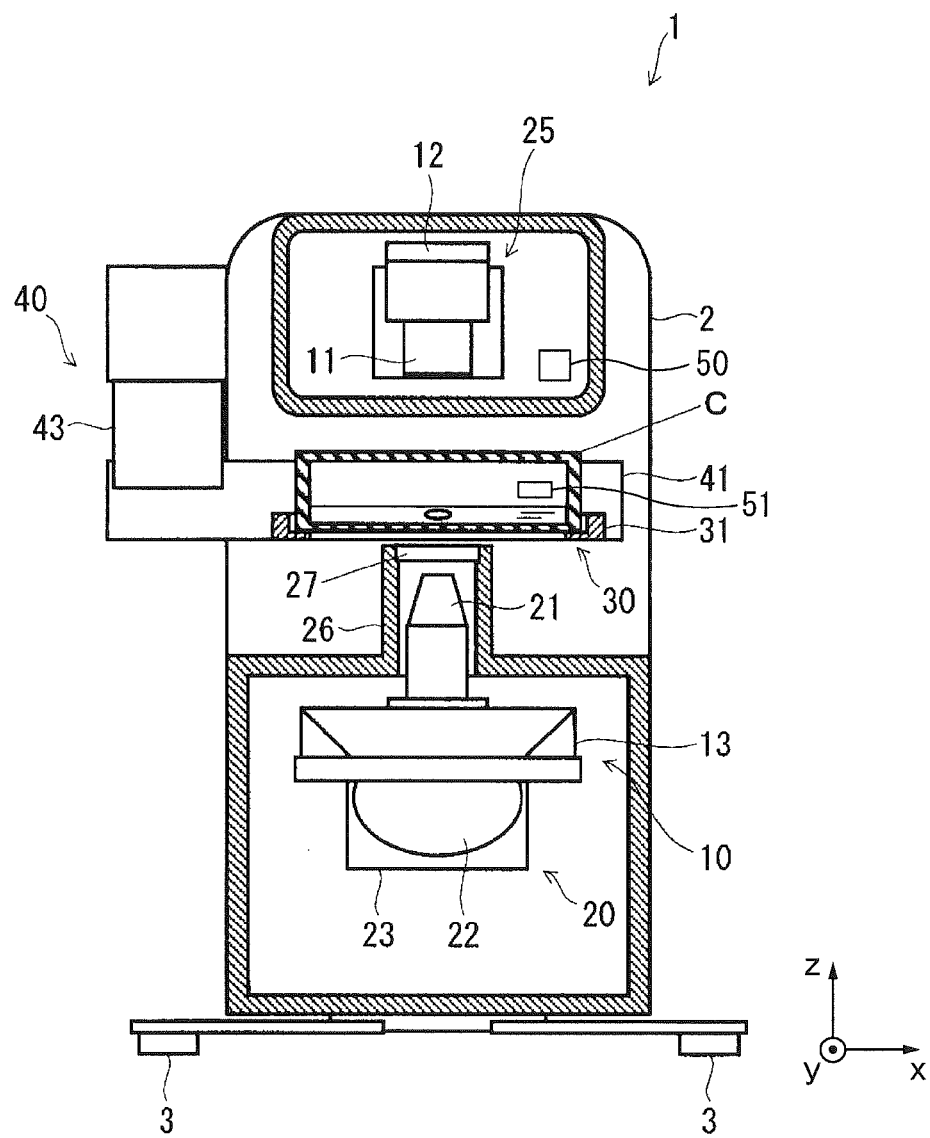
FIG. 3 is a perpendicular sectional front view of an observation apparatus.
Figure 4:
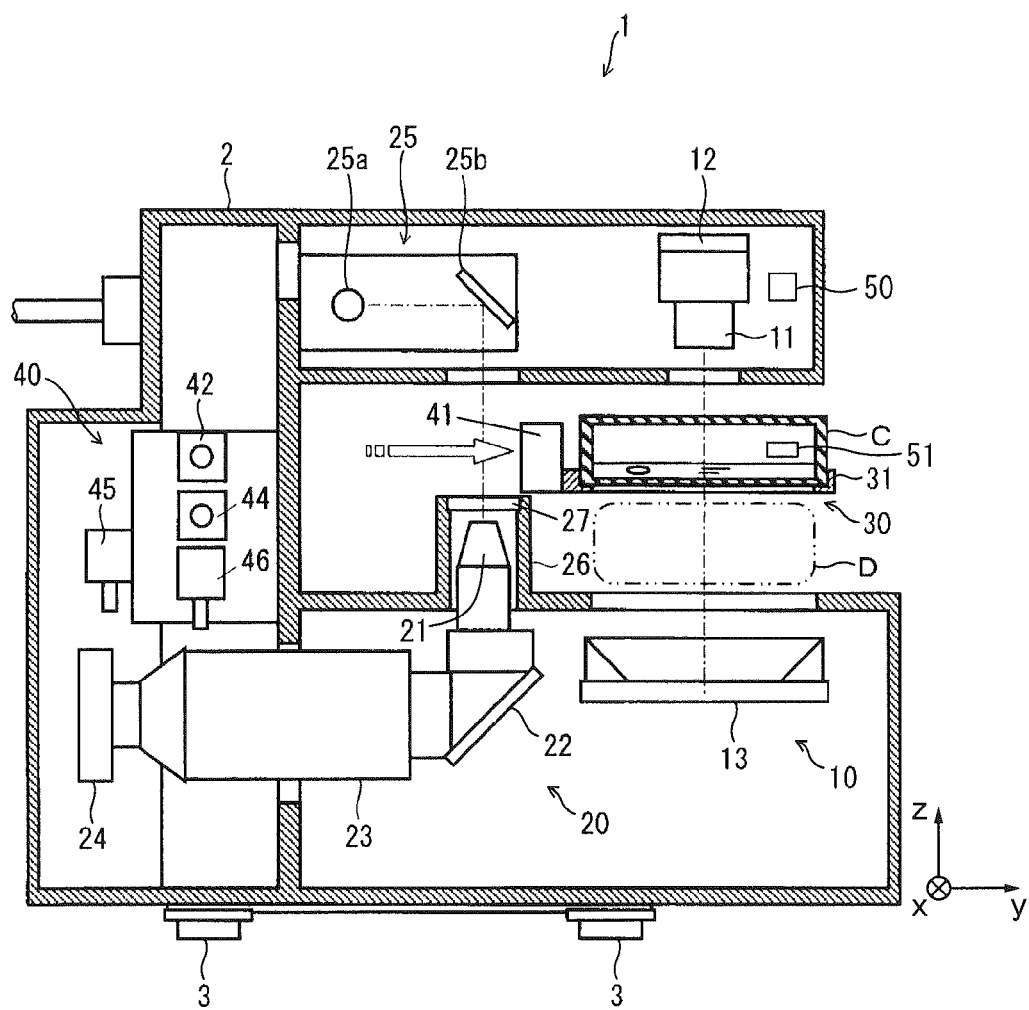
FIG. 4 is a perpendicular sectional side view of an observation apparatus and illustrates a state in which a container has been moved to a spot corresponding to a macro observation unit.
Figure 5:
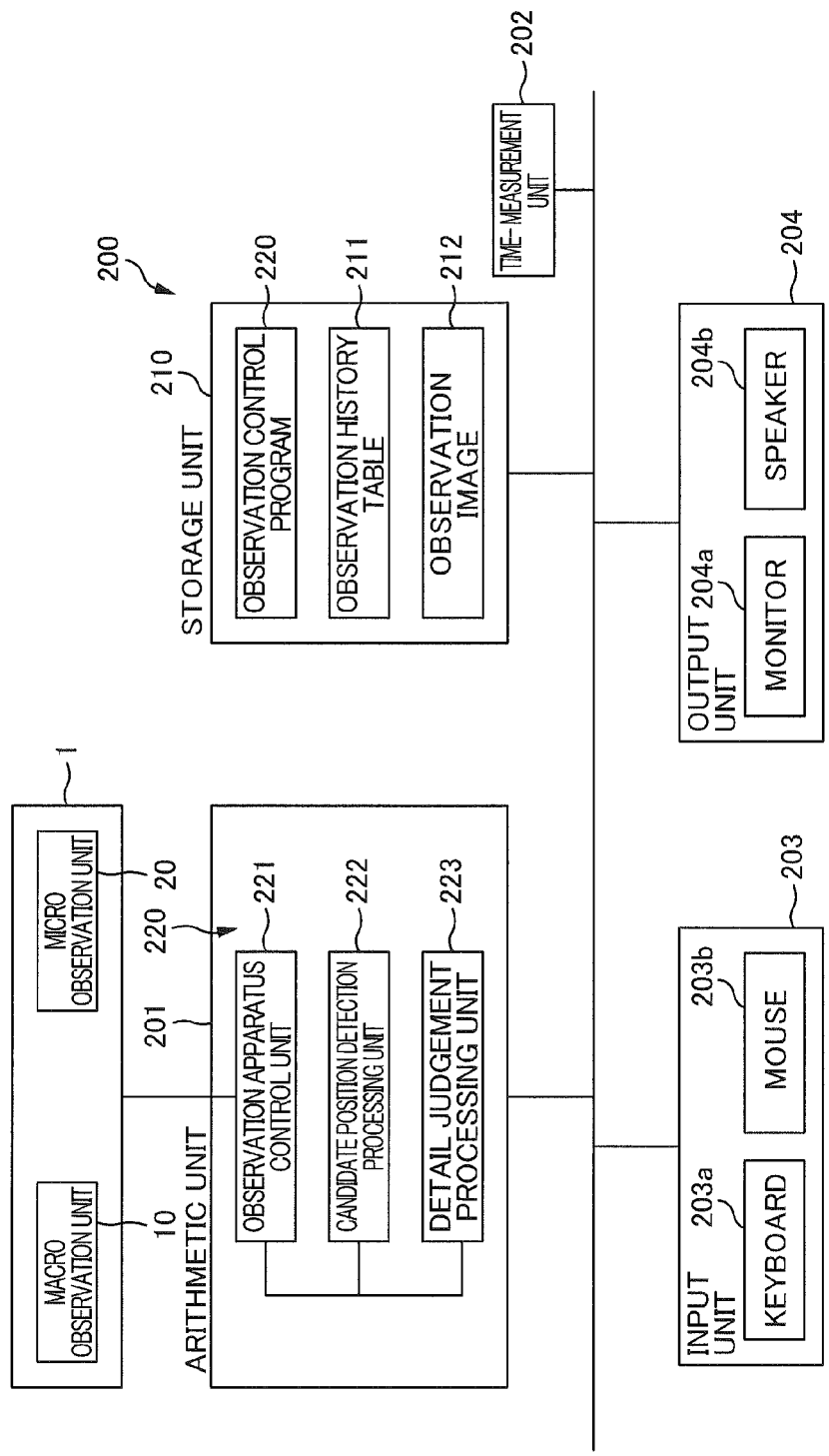
FIG. 5 is a block diagram illustrating a configuration of a computer.

An observation system S according to a first embodiment of the present invention will be described with reference to FIGS. 1 to 6. FIG. 1 is an entire configuration diagram of the observation system S, FIG. 2 is a perpendicular sectional side view of an observation apparatus 1 included in the observation system S, FIG. 3 is a perpendicular sectional front view of the observation apparatus 1, FIG. 4 is a perpendicular sectional side view of the observation apparatus 1, and FIG. 5 is a block diagram illustrating a configuration of a computer 200 included in the observation system S. FIG. 6 is a diagram illustrating an observation history table.

As illustrated in FIG. 1, the observation system S includes, for example, the observation apparatus 1, a control device 100, and the computer 200. Further, in FIG. 1, constituent elements built in the observation apparatus 1 and not seen from the outside are indicated by a broken line.

In the following description, it is assumed that a direction from the left side surface to the right side surface of the observation apparatus 1 when the observation apparatus 1 is seen from the front is the +x-axis direction; a direction from the front rear side to the front side of the observation apparatus 1 is the +y-axis direction; and a direction from a bottom surface to a top surface of the observation apparatus 1 is the +z-axis direction.

Therefore, FIG. 1 illustrates the left side surface portion of the observation apparatus 1.

<Observation Apparatus>

Though the details will be described later, the observation apparatus 1 is a device including: a macro observation unit 10 (entire image pickup unit) configured to pick up an image of an entire sample such as a cell contained in a container C; a micro observation unit 20 (magnifying image pickup unit) configured to magnify and pick up an image of a part of the sample in the container C; a conveying unit 30 on which the container C is placed; a driving unit 40 configured to move the conveying unit 30 in the x-axis direction and the y-axis direction; and an IC tag reader 50.

<Computer>

The computer 200 is a device configured to control the whole of the observation system S. The computer 200 is a device including a CPU (Central Processing Unit) and memory, and is configured to control the observation system S according to an embodiment of the present invention by executing an observation control program 220 which will be described later.

Though the details will be described later, a sample such as a cell cultured in the container C is imaged by using the observation apparatus 1 every predetermined period of time, such as once a day. The computer 200 first instructs the observation apparatus 1 to pick up an image of the whole of the container C placed on the conveying unit 30. Then, the computer 200 obtains an image obtained by picking up an image of this entire container C (macro observation image) from the observation apparatus 1, and performs a predetermined image analysis, thereby identifying a location of the cell mass which is being formed in the container C.

Then, the computer 200 specifies the location of each cell mass identified as above and causes the observation apparatus 1 to magnify and pick up an image of a portion of each cell mass. The computer 200 obtains an image obtained by magnifying and picking up an image of each cell mass (magnified observation image) from the observation apparatus 1, and displays it on a monitor 204a and/or records it in a storage device such as a hard disk device.

<Control Device>

The control device 100 is a device configured to control the macro observation unit 10, the micro observation unit 20, the driving unit 40, and the IC tag reader 50, for example, of the observation apparatus 1 by obtaining various commands outputted from the computer 200 in order to control the observation apparatus 1. The control device 100 includes a driver and a controller, not shown, for driving the observation apparatus 1.

A configuration may be such that, for example, the computer 200 or the observation apparatus 1 includes a function of the control device 100 as well and the observation system S does not include the control device 100. Further, a configuration may be such that, for example, the observation apparatus 1 includes functions of the control device 100 and the computer 200 as well and the observation system S does not include the control device 100 or the computer 200.

<Container C>

The container C is a container made of transparent glass, for example, formed having a circular bottom surface and a side surface surrounding the bottom surface, for example. The container C is attached, for example, on the side surface thereof, with an IC tag 51 having identification information of the container C recorded therein. A label on which a barcode indicating the identification information of the container C is printed may be attached on the side surface of the container C. The identification information of the container C is read by the IC tag reader 50 of the observation apparatus 1 in response to an instruction from the computer 200.

The container C is provided with a lid so as to prevent contamination from the exterior or contamination with other containers.

==Observation Apparatus==

The observation apparatus 1 will be described in detail.

As illustrated in FIGS. 1 to 4, the observation apparatus 1 includes, in a main body 2 which is housing thereof, the macro observation unit 10, the micro observation unit 20, the conveying unit 30, the driving unit 40, and the IC tag reader 50.

The macro observation unit 10 is configured to pick up an image of the whole of the cells in the container C, which contains the cells and a culture fluid for the cells and arranged on the conveying unit 30, based on an instruction from the computer 200.

The micro observation unit 20 is configured to magnify and pick up an image of a portion of the cells in the container C, containing the cells and a culture fluid for the cells, arranged on the conveying unit 30, based on an instruction from the computer 200.

The conveying unit 30 is configured to hold the container C.

The driving unit 40 is configured to move the conveying unit 30 in the fore-and-aft direction (y-axis direction) and the left-and-right direction (x-axis direction), and stop it at a desired position based on an instruction from the computer 200.

The main body 2 is supported by leg portions 3 provided at 4 spots with respect to a floor surface.

The IC tag reader 50 is configured to read the identification information of the container C from the IC tag 51 attached to the container C that is placed on the conveying unit 30, based on an instruction from the computer 200.

<Macro Observation Unit>

The macro observation unit 10 is provided at a portion on the front side of the interior of the sealed housing of the main body 2, and includes a lens 11 which is a macro observation optical system, a CMOS camera 12 which is an image pickup unit, and a ring illumination 13 which is a macro observation illumination.

The lens 11 is arranged above a movement space of the conveying unit 30 holding the container C and is provided so as to be capable of observing downward the interior of the container C.

The CMOS camera 12 is provided vertically above the lens 11, and is arranged such that an image pickup element surface thereof is directed to the lens 11 provided below.

The ring illumination 13 has such a configuration that a plurality of LEDs aligned in a ring shape are attached so as to be directed diagonally inward and upward, and is arranged below the movement space of the conveying unit 30. Note that a space D is provided with a predetermined distance between the ring illumination 13 and the container C of the conveying unit 30 (see FIG. 4). As a result, since a space in which air circulates is created between the ring illumination 13 and the container C, it becomes difficult for the heat generated by the ring illumination 13 to be transferred to the container C. Therefore, an influence of heat generation caused by the ring illumination 13 upon growth of the cell can be suppressed.

The ring illumination 13 projects light diagonally upward toward the center of a ring so as to illuminate the cell in the container C which is an observation target on the conveying unit 30 located above the ring illumination 13. The CMOS camera 12 and the lens 11 are arranged such that the optical axes thereof match each other, and the ring illumination 13 is arranged such that the matched optical axes passes through the center of the ring illumination 13.

With such configuration, an image of the cell in the container C illuminated by the ring illumination 13 is formed on the image pickup element surface of the CMOS camera 12 by the lens 11. The macro observation unit 10 picks up an image of the cells of the entire container C. This image is sent to the computer 200 and displayed on the monitor 204*a* as well as is stored in a recording medium such as hard disk. Thus, identification and specification of a cell mass having a plurality of cells gathering therein in the container C can be performed easily.

Further, the macro observation unit 10 projects light diagonally above onto the container C from therebelow, and thus, in the bottom surface of the container C, the light passing through a spot where the cell is present is scattered by the cell, and a part of the scattered light enters the CMOS camera 12 and the cell looks white; while the light passing through a spot where no cell is present is not scattered, and the light does not enter the CMOS camera 12 and the cell looks black.

As such, it is possible to project appropriate light for identifying the cell emerging and growing in the vicinity of the inner bottom surface of the container C. Then, such a contrast can be obtained, by which the external shape of the cell can be recognized as a white mass. Projection of the light from below produces such an effect of preventing which the observation becomes impossible due to blown-out highlights of the cell that are caused by light reflected by the lid of the container C.

<Micro Observation Unit>

The micro observation unit 20 is a so-called phase-contrast microscope, provided in the rear of the macro observation unit 10 in the interior of the sealed housing of the main body 2, and includes: a micro observation optical system such as an objective lens 21, a reflective mirror 22, and a zoom lens 23; a CCD camera 24 which is an image pickup unit; and a phase-contrast illumination unit 25 which is a micro observation illumination.

The objective lens 21 is arranged below the movement space of the conveying unit 30, and is provided so as to be capable of observing upward in the interior of the container C. Note that, in the periphery of the objective lens 21 that is a lens unit closest to the bottom surface of the container C, an objective lens cover 26 is provided which is a cover member configured to prevent the heat generated in the lower part of the main body 2 from influencing the container C. Further, a window unit 27 is provided in an end of the upper part of the objective lens cover 26 between the objective lens 21 and the container C.

The reflective mirror 22 is arranged below the objective lens 21, and provided with such an inclination as to reflect light substantially horizontally backward. The reflective mirror 22 guides an image obtained from the objective lens 21 to the zoom lens 23 at the rear.

The zoom lens 23 is arranged in such a manner as to extend in the fore-and-aft direction (y-axis direction) to the rear of the reflective mirror 22, and is configured to magnify an image obtained from the objective lens 21.

The CCD camera 24 is provided in the further rear of the zoom lens 23, and is arranged such that an image pickup element surface thereof is directed toward the zoom lens 23 in the front.

The phase-contrast illumination unit 25 is provided in the upper part of the main body 2, and includes an LED 25*a* and a reflective mirror 25*b*. The LED 25*a* irradiates, with light, the cell to be observed in the container C on the conveying unit 30 located below the phase-contrast illumination unit 25. The reflective mirror 25*b* is arranged vertically above the objective lens 21, and is configured to reflect light so that the light projected by the LED 25*a* reaches the objective lens 21 via the container C.

With such configuration, an image of the cell in the container C irradiated by the phase-contrast illumination unit 25 is formed on the image pickup element surface of the CCD camera 24 by the objective lens 21, the reflective mirror 22, and the zoom lens 23. Then, the micro observation unit 20 magnifies and picks up an image of the cell in a part of an area of the container C. This image is sent to the computer 200 and displayed on the monitor 204a as well as stored in the recording medium. Thus, identification and specification of a cell mass having a plurality of cells gathering therein in the container C can be performed easily.

Further, since the relatively heavy micro observation optical system, including a plurality of the lenses and the zoom mechanisms thereof to magnify and observe a cell, is arranged in the lower part, resulting in an appropriate weight balance of the observation apparatus 1, thereby being able to make stable micro observation. Further, since the objective lens 21 can be brought closer from below the container C toward the cell that emerges and grows in the vicinity of the inner bottom surface of the container C, a focal distance is reduced, thereby being able to observe the cell at relatively great magnification. Further, since the observation is made from below the container C in the micro observation unit 20, observation can be made without being affected by stains on the lid of the container C.

<Conveying Unit>

The conveying unit 30 is provided at the front center part of the main body 2, in such a manner as to be sandwiched by the ring illumination 13 of the macro observation unit 10 as well as the magnified observation optical system of the micro observation unit 20, which are disposed below; and the macro observation optical system of the macro observation unit 10 as well as the phase-contrast illumination unit 25 of the micro observation unit 20, which are disposed above.

The conveying unit 30 includes a holder 31, and this holder 31 holds the container C containing the cells to be observed and the culture fluid for the cells. The holder 31 is positioned with respect to the macro observation unit 10 and the micro observation unit 20, and the container C is positioned with respect to the holder 31. As a result, even if the container C and the holder 31 are removed together and the culture fluid is replaced or a reagent is charged, the same spot can be easily observed both in the macro observation unit 10 and the micro observation unit 20.

<Driving Unit>

The driving unit 40 is provided in the rear and on the side of the conveying unit 30, and includes an x-axis driving mechanism 41, an x-axis motor 42, a y-axis driving mechanism 43, a y-axis motor 44, an optical system moving motor 45, and a zoom motor 46.

The x-axis driving mechanism 41 is arranged immediately rear of the conveying unit 30 as well as directly supports the conveying unit 30. The x-axis driving mechanism 41, including a belt, a pulley, a slide guide member, and a shaft, not shown, is driven by the x-axis motor 42, and moves the conveying unit 30 in the left-and-right direction.

The y-axis driving mechanism 43 is arranged in a place on the side surface of the conveying unit 30 and the main body 2, and supports the x-axis driving mechanism 41. The y-axis driving mechanism 43, including a belt, a pulley, and a slide guide member, not shown, is driven by the y-axis motor 44, and moves the conveying unit 30 in the fore-and-aft direction together with the x-axis driving mechanism 41 (See FIG. 4).

By operating such driving mechanisms, the conveying unit 30 conveys the container C from the macro observation unit 10 to the micro observation unit 20 or in the opposite direction. Since the container C is moved, even if the macro observation unit 10 and the micro observation unit 20 are arranged at places far from each other, it becomes possible to observe the entire container C and identify an emerging cell mass, and further, magnify and observe this identified cell mass in detail.

The conveying unit 30 is configured to convey the container C in a direction orthogonal to the optical axis direction of the macro observation unit 10 and the micro observation unit 20 as described above, and by making common at least one direction in the conveying directions, i.e., the fore-and-aft direction, therebetween, coordinates in the observation field of view in the macro observation unit 10 is matched with coordinates in the observation field of view in the micro observation unit 20.

Thus, the coordinates in the observation fields of view in the macro observation unit 10 and the micro observation unit 20 match each other, thereby being able to easily identify, using the micro observation unit 20, the cell mass specified through the observation of the entire container C by the macro observation unit 10. Therefore, it is prevented to erroneously identify a target cell mass, thereby being able to realize observation with high accuracy.

The optical system moving motor 45 and the zoom motor 46 are arranged in the main body 2 in the rear of the conveying unit 30. The optical system moving motor 45 is a motor configured to move the magnified observation optical system and the CCD camera 24 in the up-and-down direction. The zoom motor 46 is a motor configured to change a magnification of the zoom lens 23, and is capable of changing magnification of an image to be picked up.

<IC Tag Reader>

The IC tag reader 50 is provided in a part on the front side in the interior of the sealed housing of the main body 2, for example. The IC tag reader 50 is configured to oscillate an electromagnetic wave at a predetermined frequency and read identification information of the container C from a response wave received from the IC tag 51 that is attached to the container C, based on an instruction from the computer 200.

==Computer==

The computer 200 includes an arithmetic unit 201, a storage unit 210, a time-measurement unit 202, an input unit 203, and an output unit 204, as illustrated in FIG. 5.

The arithmetic unit 201 includes a CPU, a microcomputer, and other electronic components, and is realized by, for example, the CPU executing an observation control program 220 stored in the storage unit 210. The arithmetic unit 201 is configured to control a series of observation operations relating to the observation apparatus 1.

The arithmetic unit 201 includes an observation apparatus control unit 221, a candidate position detection processing unit 222, and a detail judgment processing unit 223, as illustrated in FIG. 5 as a functional block.

<Observation Apparatus Control Unit>

The observation apparatus control unit 221 sends an instruction to the IC tag reader 50 of the observation apparatus 1 and reads the identification information of the container C from the IC tag 51 attached to the container C that is placed on the conveying unit 30.

Further, the observation apparatus control unit 221 sends an instruction to the macro observation unit 10 of the observation apparatus 1, and causes it to pick up an image of the entire container C, thereby obtaining the image of the entire container C (macro observation image).

Further, the observation apparatus control unit 221 notifies the macro observation image to the candidate position detection processing unit 222, and causes the candidate position detection processing unit 222 to identify the position of each cell mass emerging in the container C.

Further, the observation apparatus control unit 221 obtains coordinates describing the position of each cell mass identified by the candidate position detection processing unit 222 from the candidate position detection processing unit 222, sends an instruction to the micro observation unit 20 of the observation apparatus 1, and causes the micro observation unit 20 to magnify and pick up an image of a portion of each cell mass in the container C, thereby being able to obtain a magnified image (magnified observation image) of each cell mass.

Further, the observation apparatus control unit 221 acquires an estimated position of the cell mass in the container C based on a past observation history recorded in an observation history table 211, which will be described later, while waiting for an identification result of the position of each cell mass in the container C sent from the candidate position detection processing unit 222. And this estimated position is sent to the micro observation unit 20 of the observation apparatus 1, and the micro observation unit 20 is caused to pick up a magnified observation image in the vicinity of the estimated position.

Note that the vicinity of the estimated position indicates a part of an area in the container C including the aforementioned estimated position, and an area including surroundings of a sample mass corresponding to a field of view of the magnified observation image which is picked up such that the whole or the most of a sample mass fits therein. For example, in micro observation using a cell mass as a target, an image containing about one to adjacent several cell masses in the field of view is usually suitable for identifying the cell mass or determining its state.

Further, the observation apparatus control unit 221 obtains a macro observation image or a magnified observation image of the container C picked up by the observation apparatus from the observation apparatus 1, and stores it as an observation image 212 in the storage unit 210.

Further, when a magnified observation image is picked up, the observation apparatus control unit 221 records, in the observation history table 211 illustrated in FIG. 6, the identification information of the container C whose magnified observation image has been picked up; coordinates describing the position at which the image has been picked up; the date when the image has been picked up; and information indicating that the magnified observation image has been picked up ("Y" is written in a magnified image pickup column), in association with one another. Note that the "information indicating that the magnified observation image has been picked up" is also described as "information indicating that an image of the sample mass has already been picked up".

<Candidate Position Detection Processing Unit>

The candidate position detection processing unit (also referred to as a sample mass identification unit) 222 analyzes the macro observation image obtained from the observation apparatus control unit 221 with a predetermined algorithm and identifies a position of each cell mass.

Then, the candidate position detection processing unit 222 notifies a list of coordinates describing the position of each of the identified cell masses to the observation apparatus control unit 221.

Further, when identifying the position of each cell mass, the candidate position detection processing unit 222 records, in the observation history table 211, the identification information of the container C; the coordinates describing the position of the identified cell mass; the date; and the information indicating that the position of the cell mass has been identified ("Y" is written in a position detection column) in association with one another.

There are various algorithms here that are used when the candidate position detection processing unit 222 identifies the position of a cell mass.

In an embodiment of the present invention, as will be described below, a method of finding a cell mass based on the size or density of a white pixel area after the macro observation image is subjected to binarization process (image thresholding), will be described as an example.

The candidate position detection processing unit 222 first converts an image into a gray image if it is a color image, and then, discriminates using a predetermined threshold value between a part excluding a cell mass and a part corresponding to a cell mass in the image picked up through the entire image-pickup process. As a result, binarization is executed such that the part excluding a cell mass is changed into black and the part corresponding to a cell mass is changed into white. Then, the cell, that is, the number of white pixels is calculated. A method of calculating the number of white pixels includes: a labeling method of calculating a connected area of white pixels; and a small-area method of calculating an area so that the number of white pixels in a small area which is predetermined at an arbitrary position, becomes as great as possible, for example.

The labeling method is a method of identifying a cell mass by the size of a single white-pixel area or the degree of the white-pixel-area density, while the small area method is a method of identifying a cell mass by the number of the white pixel areas or the greatness of the number thereof, and the degree of the density. In addition, identification may be made by the degree of isolation of the cell masses (the degree at which individual cell masses exist with a predetermined distance one another). Note that the labeling method is employed herein.

The labeling process is a process of grouping a plurality of pixels by assigning the same number (label) to white pixels (or black pixels) adjacent to each other, with respect to the image subjected to the binarization process. In judgment on adjacency in the labeling process, four-connection (four-neighbor) and eight-connection (eight-neighbor) are used. In the four-connection, if a pixel is contiguous to the pixel of attention in the up-and-down or left-and-right direction, they are judged to be adjacent, while in the eight-connection, judgment on adjacency is made by further considering contiguousness in additional four diagonal directions. As such, the candidate position detection processing unit 222 identifies a mass of binarized white pixels, i.e., a cell mass, from an image that has been picked up through the entire image-pickup process.

Then, the candidate position detection processing unit 222 recognizes, as a micro observation target, a cell mass having a size equal to or greater than a predetermined size among identified cell masses. The "predetermined size" indicates a size set in advance for a cell mass, and such a size that can be judged to be observed under magnification. The predetermined size is set here at 1000 pixels for the number of pixels, for example, and is stored in the storage unit 210. As a result, a cell mass having the number of pixels equal to or greater than 1000 pixels is recognized as a micro observation target cell mass, thereby being able to determine the time of emergence of a cell mass. Therefore, it becomes possible to perform continuous observation from the time of emergence of a cell mass to the time of completion of growth thereof.

Further, the candidate position detection processing unit 222 executes sorting of the masses of white pixels in decreasing order of the number of pixels. Then, the candidate position detection processing unit 222 selects, as observation targets, the predetermined number of cell masses in decreasing order of the number of pixels, for example, and detects coordinates of the center of a mass of white pixels.

Next, the candidate position detection processing unit 222 converts the coordinates by pixels on an image picked up through the entire image pickup processing into a real scale with the center of the image set as the origin. Various aberrations such as distortion aberration of the image may be corrected here. Further, the candidate position detection processing unit 222 converts the real scale into the motor pulse numbers of the x-axis motor 42 and the y-axis motor 44 of the driving unit 40 in the observation apparatus 1, so as to be matched with a position on the image expressed by this real scale. As such, the candidate position detection processing unit 222 creates a common coordinate system in which the coordinates on the image picked up through the magnifying image-pickup process matches the coordinates on the image picked up through the entire image-pickup process.

Then, the candidate position detection processing unit 222 notifies this list of the coordinates to the observation apparatus control unit 221.

Note that, a method called generalized Hough transform can be used as an algorithm used when the candidate position detection processing unit 222 identifies the position of the cell mass, for example, in another case where the shape of an observation target can be expressed by a numerical formula using the relatively small number of parameters such as a circle or an ellipse.

Alternatively, if an exemplified image illustrating a typical example of an observation target can be prepared, a method called template matching can be used of detecting a spot similar to the exemplified image by repeating matching a part of the entire image against the exemplified image while shifting a matching position.

In any method, the candidate position detection processing unit 222 according to an embodiment of the present invention is configured to prevent missing detection by detecting extra cell masses in the container C as well as enable detection processing to be completed in a short time.

Though details will be described later, the detail judgment processing unit 223 judges afterward whether or not the cell mass detected by the candidate position detection processing unit 222 is worth a cell mass to be observed.

With such a configuration, while processing of detecting a cell mass is executed by the candidate position detection processing unit 222 swiftly without missing, a cell mass to be observed can be accurately identified by the detail judgment processing unit 223.

<Detail Determination Processing Unit>

The detail judgment processing unit 223 is configured to judge whether or not each cell mass detected by the candidate position detection processing unit 222 is worth a cell mass to be observed.

Further, when the detail judgment processing unit 223 has made a judgment with respect to the cell mass, the detail judgment processing unit 223 records, in the observation history table 211, the identification information of the container C, the coordinates describing the position of the determined cell mass, the date, and the information indicating the judgment result of the cell mass. When the detail judgment processing unit 223 has judged that the cell mass truly deserve a cell mass to be observed, the detail judgment processing unit 223 records "Y" in a detail judgment column of the observation history table 211. Whereas, when the detail judgment processing unit 223 has judged that the cell mass does not truly deserve a cell mass to be observed, the detail judgment processing unit 223 records "N" in the detail judgment column of the observation history table 211.

Since the magnified observation image contains more detailed information as compared with the macro observation image, the detail judgment processing unit 223 can accurately judge whether or not each cell mass is truly worth an observation target.

There are various algorithms here that are used when the detail judgment processing unit 223 judges whether or not the cell mass is truly worth a cell mass to be observed.

In an embodiment of the present invention, a method using the template matching will be described as an example as follows.

First, the detail judgment processing unit 223 extracts an image of a judgment-target cell mass from the magnified observation image.

Then, the detail judgment processing unit 223 performs matching of a patch image prepared in advance with a magnified observation image. As a matching result, a range image, which is expressed by shading, between the magnified observation image and the patch image is obtained.

The detail judgment processing unit 223 executes binarization processing for the range image by using a predetermined threshold value. Matching methods include template matching, histogram matching, for example, and a judgment target image, i.e., a magnified observation image, is subjected to raster scan with the patch image, thereby calculating the range therebetween. If a large number of patch images are prepared, the range images of the matching results are integrated. Note that even if a plurality of cell masses are present in the magnified observation image, the detail judgment processing unit 223 can identify each of the cell masses separately.

Subsequently, the detail judgment processing unit 223 detects a contour by executing contour extraction, performed with an edge extraction filter, and contour tracing, performed through eight-connection search, for example, in an image subjected to the binarization processing. As the edge extraction filter for contour extraction, a differential filter, a Prewitt filter, a Sobel filter, a Canny Edge Detector can be used, for example. In the contour tracing, a contour line can be extracted by tracing contour points sequentially in one direction from a tracing start point of a contour, and four-connection search can be also used.

Then the detail judgment processing unit 223 detects a predetermined shape, such as a circle, an ellipse, a rectangle, from the contour detection results. As a method of detecting a circle from a contour or an edge, Hough transform can be used. As a method of detecting an ellipse from a contour or an edge, generalized Hough transform or a method of fitting an ellipse to a sequence of points of a contour using least squares estimation can be used. As a method of detecting a rectangle from a contour or an edge, a method of fitting a rectangle so that all the sequences of points in a contour are included, can be used. As such, the detail judgment processing unit 223 extracts a contour of a cell mass from a magnified observation image and identifies a shape thereof.

Subsequently, the detail judgment processing unit 223 judges whether or not the cell mass has a predetermined shape. The "predetermined shape" is a shape set in advance for a cell mass, and is preferably such a shape that can be judged to have a high possibility of continuously growing in a manner suitable for observation and, for example, is close to a circle to the highest degree possible.

As the criteria for judging a cell mass to be of a predetermined shape, criteria such as a size and the degree of unevenness may be added to the shape, for example. The criteria for judging a shape includes the degree of ellipse of an ellipse surrounding the contour, and roundness of a circle surrounding the contour, for example. The criteria for judging a size includes a size of a white pixel mass, a length of a contour of a white pixel mass, the area of the interior of a contour of a white pixel mass, a length of a long axis of an ellipse, a length of a short axis of an ellipse, a length of a circumference of an ellipse, a diameter of a circle, a length of a circumference of a circle, a length of a rectangle surrounding the contour, and the area of a rectangle surrounding the contour, for example. The criteria for judging the degree of unevenness includes the ratio of the area of the contour to a peripheral length, the ratio of the area of the contour to the area of a rectangle surrounding the contour, the ratio of the length of the contour to the length of the rectangle surrounding the contour, the number of corners in the contour, the ratio of the area of the contour to the area of a circle or an ellipse surrounding the contour, the ratio of the length of the contour to the length of a circumference of a circle or a circumference of an ellipse surrounding the contour, the ratio of the area of a rectangle surrounding the contour to the area of a circle or an ellipse surrounding the contour, and the ratio of the length of a rectangle surrounding the contour to the length of a circle or an ellipse surrounding the contour, for example. As a method of corner detection when judgment is made based on the number of corners in a contour, Harris corner detection and SUSAN operator can be used, for example.

The criteria for judging the predetermined shape of a cell mass is set here at the degree of ellipse equal to or smaller than 1.1, for example, and is stored in the storage unit 210. The degree of ellipse is the ratio of the long-axis length of the ellipse to the short-axis length thereof. As a result, a cell mass close to a circle to the highest degree possible is identified, thereby being able to automatically select a cell mass having an appropriate shape for continuing observation. As a result, it becomes possible to lower the observation priority of a cell mass that has grown in a distorted shape during a growing process, or stop the observation thereof, and thus observation of a cell mass having an appropriate shape can proceed more efficiently.

Further, not only a method of explicitly judging a shape by a threshold value (e.g., the degree of ellipse of 1.1), but such a method can be used that cell mass images are sorted based on superiority of judgment results and displayed on a monitor 204a (in the case of the degree of ellipse, they are displayed in order from the smaller degree of ellipse), thereby leaving, to a user, the judgment of the range within which the cell mass is considered suitable.

Then, the detail judgment processing unit 223 records the judgment result of the cell mass in the observation history table 211.

As another algorithm used when the detail judgment processing unit 223 make judgment with respect to a cell mass, such a method may be used, for example, that a magnified observation image is divided into the predetermined number of areas in advance, a predetermined attribute for each of the areas (color information and a shape and a position of the area) is accumulated as an index, and judgment is made by generating a similar index for the magnified observation image to be judged and by comparing the both.

Further, the detail judgment processing unit 223 may be configured to output a judgment result on whether or not the cell mass is an observation target as a continuous value indicating a degree of certainty that the cell mass is an observation target, instead of a binary value such as Yes or No.

In this case, though details will be described later, in processing of giving priority for photographing a magnified observation image based on an observation history, it becomes also possible to more appropriately execute acquisition of a magnified observation image, which is to be performed precedently, by giving higher priority to a cell mass with a greater degree of certainty, for example, based on the degree of certainty outputted by the detail judgment processing unit 223.

<Storage Unit>

The storage unit 210 is a recording medium for storing various types of data relating to observation of a cell and an operation of the observation system S. The storage unit 210 includes a hard disk device and a semiconductor memory, for example.

As illustrated in FIG. 5, the storage unit 210 stores the observation control program 220, the observation history table 211, and the observation image 212.

The observation history table 211 is illustrated in FIG. 6. The observation history table 211 stores the identification information of the container C (container No.), the coordinates of each cell mass in the container C, the date when each cell mass has been observed (time and date information), and an observation result (presence or absence of position detection, presence or absence of magnifying image pickup, and a detail judgment result) in association with one another.

As described above, in the observation history table 211, the observation histories are kept by the observation apparatus control unit 221, the candidate position detection processing unit 222, and the detail judgment processing unit 223, respectively. When keeping the observation histories in the observation history table 221, the observation apparatus control unit 221, the candidate position detection processing unit 222, and the detail judgment processing unit 223 keep the observation histories of the same time and date for the same cell mass in the same record, by judging identity of observation histories using an entry in the container number column, an entry in the cell mass coordinate column, and an entry in the date column.

<Time-Measurement Unit>

The time-measurement unit 202 is configured to measure time relating to period of time and days from start of observation of a cell and operation control of the observation system S, thereby being able to grasp various types of time period.

<Input Unit>

The input unit 203 includes pointing devices such as a keyboard 203a and a mouse 203b. The user inputs characters and numerical values by using the keyboard 203a. Further, the user moves a cursor in an arbitrary direction on a screen of the monitor 204a of the output unit 204 by using the mouse 203b, and selects a menu or other options. The arithmetic unit 201 is configured to execute various types of processes to a program, data, and a file stored/inputted in/to the arithmetic unit 201 and the storage unit 210, based on information obtained from the input unit 203, and execute an output process to the output unit 204.

<Output Unit>

The output unit 204 includes: the monitor 204a such as a liquid crystal display and a CRT; and a speaker 204b, for example. The arithmetic unit 201 is configured to cause a window, an icon, and a menu to be displayed on the monitor 204a based on the executed process of a program, and cause sound to be emitted from the speaker 204b. Further, the arithmetic unit 201 is configured to cause characters and numerical values inputted by the user to be displayed on the monitor 204a based on the information from the input unit 203, and cause a cursor, which is to be moved by the user, to be displayed.

==Flow of Processing==

<Operation Flow>

Figure 7:
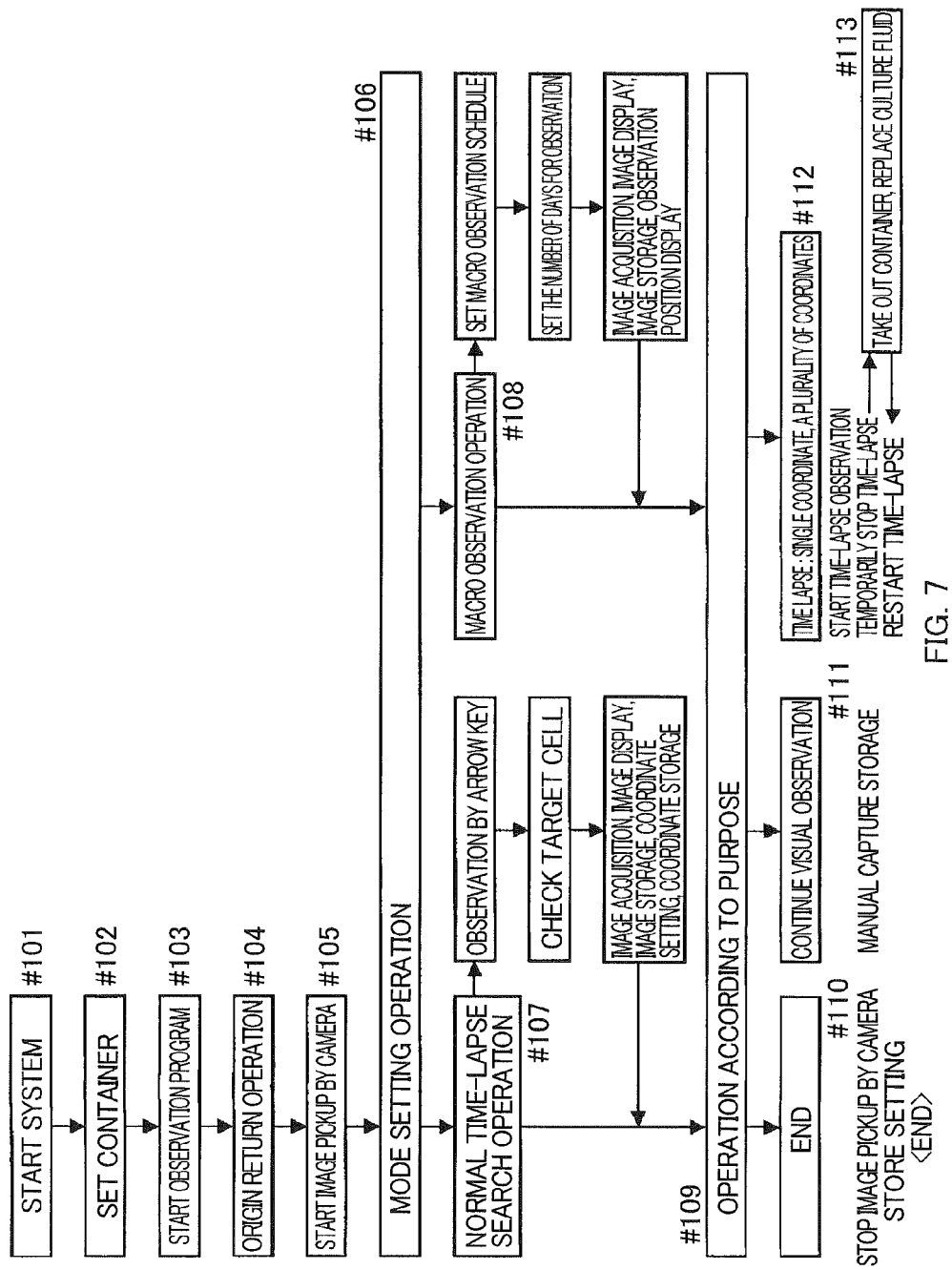
FIG. 7 is an explanatory diagram illustrating a flow according to an operation of the observation system.

Subsequently, an operation of the observation system S performed by the user relating to observation of a cell in the container C will be described along a flow illustrated in FIG. 7. FIG. 7 is an explanatory diagram illustrating the flow relating to an operation of the observation system S.

The user first turns on the observation apparatus 1, the control device 100, and the computer 200, thereby starting the observation system S (Step #101 in FIG. 7). Then, the user sets the container C containing a cell and a culture fluid for the cell on the holder 31 of the conveying unit 30 (Step #102). Subsequently, the user starts the observation program 220 in the computer 200 (Step #103), thereby displaying an operation screen on the monitor 204a.

The observation program 220 is configured to perform an origin return operation of the conveying unit 30 automatically together with startup of the program (Step #104). Then, the observation program 220 is configured to start picking up an image with a camera (Step #105), and to display a real-time image from the camera on the monitor 204a.

Subsequently, the user executes a mode setting operation (Step #106). In this mode setting operation, it is possible to select between a normal time-lapse search operation (Step #107) and a macro observation operation (Step #108). The time lapse observation is a method of observing a position, set in advance, in every predetermined time period.

In the normal time-lapse search operation (Step #107), the user observes the interior of the container C while moving the container C using an arrow key on the monitor 204a or the keyboard 203a, and checks a target cell. Then, the user executes acquisition, display and storage of a captured image, and further executes setting of coordinates and storage of the coordinates.

In the macro observation operation (Step #108), the user sets the predetermined identification time period and the predetermined number of days for identification in the macro observation. The acquisition, display and storage of the image and further the observation position display are automatically executed based on setting.

Subsequently, in an operation according to purpose (Step #109), it is possible to select from operations of end (Step #110); continuation of visual observation (Step #111); and time lapse (Step #112).

If the end (step #110) is selected, the image pickup by camera is stopped, and the setting is stored. If the continuation of visual observation (Step #111) is selected, it is possible to manually store capture of an image picked up by the camera.

If the time-lapse (Step #112) is selected, operations of starting the time-lapse observation, temporarily stopping time-lapse, and restarting time-lapse can be further performed. If the time lapse is temporarily stopped, works such as taking-out the container C, replacing the culture fluid can be performed (Step #113).

Performing the time-lapse observation using such observation program 220 enables automatic execution of such a series of processes, in which a cell mass having emerged is identified in an image picked up in the entire image-pickup process; the position thereof is specified; a shape of the cell mass is identified from an image picked up in the magnifying image-pickup process; and a cell mass in an appropriate shape for continuing the observation is selected.

<Flow of Control by Observation System>

Figure 8:
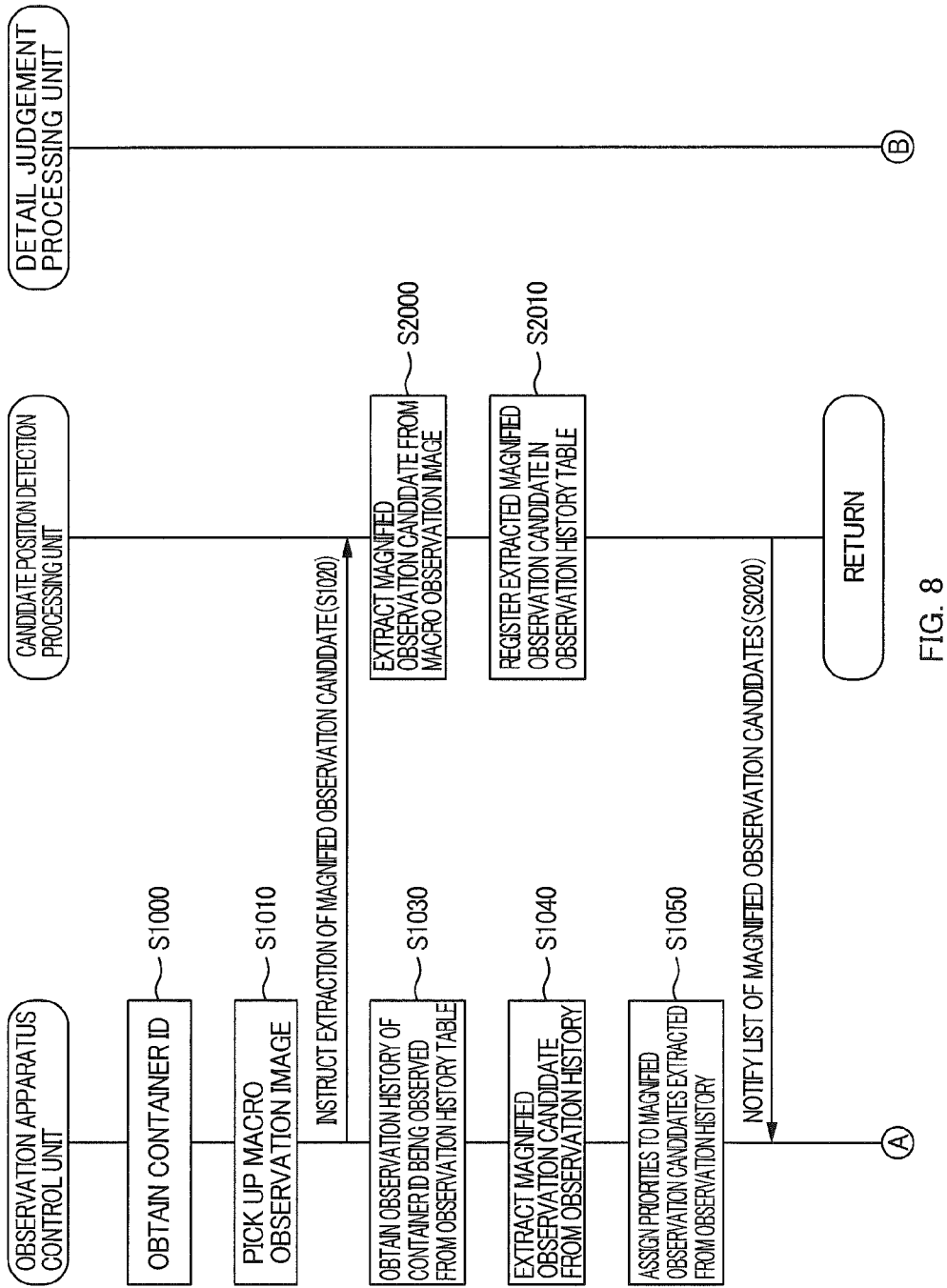
FIG. 8 is a flowchart illustrating an operation according to observation processing in an observation system.
Figure 9:
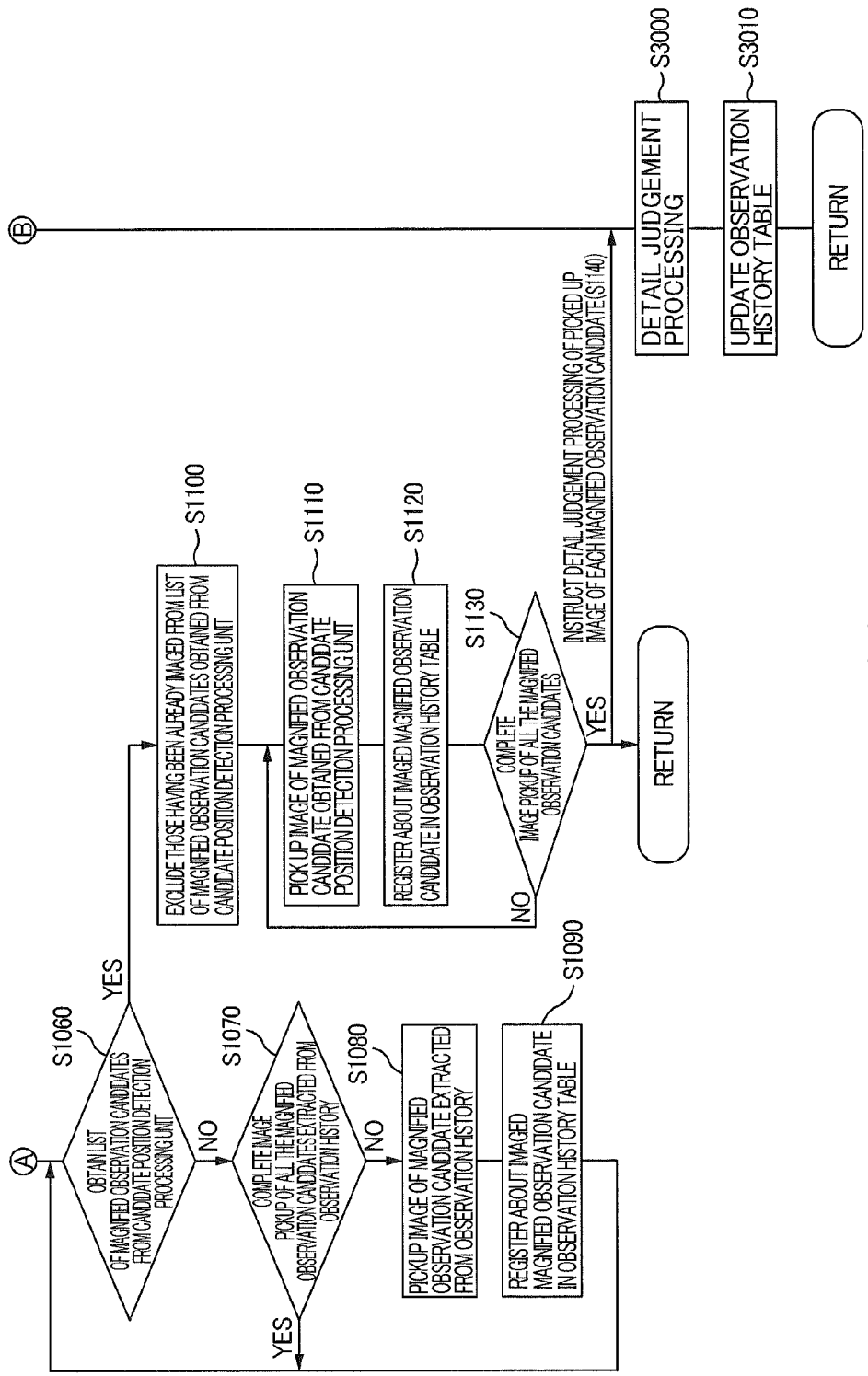
FIG. 9 is a flowchart illustrating an operation according to observation processing in an observation system.

Subsequently, a flow of control executed by the observation system S according to an embodiment of the present invention will be described with reference to flowcharts illustrated in FIGS. 8 to 9.

First, the observation apparatus control unit 221 sends an instruction to the IC tag reader 50 of the observation apparatus 1 and reads the identification information of the container C from the IC tag 51 attached to the container C that is placed on the conveying unit 30 (S1000).

Then, the observation apparatus control unit 221 sends an instruction to the macro observation unit 10 of the observation apparatus 1, and obtains an image of the entire container C (macro observation image) by causing the macro observation unit 10 to pick up an image of the whole of the entire container C (S1010).

Further, the observation apparatus control unit 221 notifies the macro observation image to the candidate position detection processing unit 222 as well as sends an instruction to detect a cell mass formed in the container C as a magnified observation candidate (S1020).

Then, the candidate position detection processing unit 222 detects the cell mass and coordinates describing the position thereof from the macro observation image, thereby extracting a magnified observation candidate (S2000). Regarding the specific contents of the processing, as exemplified, the candidate position detection processing unit 222 executes processing of finding a cell mass based on the size and density of a white pixel area, after the macro observation image is subjected to binarization processing.

Then, the candidate position detection processing unit 222 records the letter "Y" indicating that the cell mass has been detected as a magnified observation candidate in the "position detection" column of the observation history table 211, as well as the container ID, the date, and the coordinate value of the cell mass (S2010).

Then, the candidate position detection processing unit 222 notifies a list of coordinates of the cell masses detected as magnified observation candidates to the observation apparatus control unit 221 (S2020).

During a time period from a time when an instruction to detect a magnified observation candidate has been sent to the candidate position detection processing unit 222 at 51020 until a time when the list of coordinates of the magnified observation candidates has been obtained at S2020, the observation apparatus control unit 221 acquires an estimated position of each of the cell masses expected to be detected as magnified observation candidates by the candidate position detection processing unit 222, based on the past observation history of the container C currently being observed, and picks up a magnified observation image of each estimated position.

As a result, the observation apparatus control unit 221 can proceed with pickup of a magnified observation image without wasting the waiting time while the magnified observation candidate is being detected by the candidate position detection processing unit 222, and can increase efficiency of operations of detecting a sample mass as an observation target from the interior of the container C and of magnifying and picking up an image of a part of the sample mass.

The observation apparatus control unit 221 assigns priorities to estimated positions by a predetermined method which will be described later, and picks up magnified observation images of the estimated positions in order of priority.

This priority is calculated so that the higher the priority of the position is, the more reliably the position is detected as a magnified observation candidate by the candidate position detection processing unit 222.

Then, when the observation apparatus control unit 221 obtains the list of coordinates of the magnified observation candidates at S2020, the observation apparatus control unit 221 picks up a magnified observation image for each of the coordinates of the rest of the magnified observation candidates after excluding from the coordinates in this list those corresponding to the aforementioned estimated coordinates as well as those whose magnified observation images have already been picked up.

That is, when the position of a sample mass has been identified by the candidate position detection processing unit 222 and when an image of the vicinity of the position has already been picked up based on the estimated position, the observation apparatus control unit 221 does not pick up an image of the vicinity of the position.

As described above, the vicinity of the estimated position indicates a part of an area in the container C including the estimated position, and the area including the surroundings of the sample mass corresponding to a field of view of a magnified observation image that is picked up such that the whole or most of a sample mass fits therein.

As a result, it becomes possible to avoid duplication of imaging of an area whose magnified observation image has been picked up earlier based on the estimated position, thereby being able to reduce time period required for observation of a single container C (time period required for pickup of a macro observation image, detection of magnified observation candidates, pickup of a magnified observation image for each magnified observation candidate, and detail judgment of each magnified observation candidate).

Further, the observation apparatus control unit 221 picks up images of estimated positions on the container C in order of priority, thereby being able to pick up magnified observation images of more magnified observation candidates in a list of coordinates of the magnified observation candidates during a time period until when this list has been obtained from the candidate position detection processing unit 222.

Descriptions will be given in order. First, the observation apparatus control unit 221 extracts a past observation history of the container C, currently being observed, from the observation history table 211 (S1030). At this time, the observation apparatus control unit 221 may extract all the observation histories from the point of time when the observation of the container C is started or may extract an observation history of the latest predetermined period (e.g., for the past 10 days), for example.

Then, the observation apparatus control unit 221 extracts a cell mass being formed in the container C as a magnified observation candidate, by sorting extracted observation histories of the container C according to the coordinates provided in the "coordinates of cell mass" columns (S1040). At this time, even if the values of the coordinates provided in the "coordinates of cell mass" columns are not the same, if a difference between the two coordinates (first position information and second position information) is within a predetermined range, for example, the observation apparatus control unit 221 estimates that these coordinates are the position information of the same sample mass and classifies them as the same magnified observation candidate.

As a result, the observation apparatus control unit 221 can estimate in advance, based on the observation history, a position with a high possibility of being identified as the position of a sample mass through analysis of the macro observation image performed by the candidate position detection processing unit 222.

Further, the observation apparatus control unit 221 may narrow down the magnified observation candidates from all the magnified observation candidates, which can be extracted by sorting observation histories according to coordinates, to the magnified observation candidates applicable to the following requirements candidates.

For example, the observation apparatus control unit 221 can classify, as magnified observation candidates, those with "Y" in the "position detection" column and "Y" in the "magnified image pickup" column in the previous n observation histories (where n is a predetermined natural number and which indicates the past n days if an observation interval is 1 day, for example).

As a result, a position of a sample mass which has been identified in the past by the candidate position detection processing unit 222 by analyzing the macro observation image as well as whose magnified observation image has been picked up, can be identified as an estimated position, and thus, a position with a higher possibility of being identified as a position of a sample mass by the candidate position detection processing unit 222 analyzing the macro observation image can be estimated in advance by the observation apparatus control unit 221 based on the observation histories.

Alternatively, the observation apparatus control unit 221 can classify, as magnified observation candidates, those with "Y" in the "position detection" column and "N" in the "magnified image pickup" column in the past n times of the observation histories.

As a result, a position of a sample mass which has been identified in the past by the candidate position detection processing unit 222 by analyzing the macro observation image but whose magnified observation image has not picked up, can be identified as an estimated position, and thus, a position of a sample mass whose magnified observation image has not been picked up yet can be estimated in advance by the observation apparatus control unit 221 based on the observation history.

Alternatively, the observation apparatus control unit 221 can classify, as magnified observation candidates, those with "Y" in the "magnified image pickup" column and "Y" in the "detail judgment" column in the past n times of the observation histories.

As a result, a position of a sample mass which has been identified in the past by the candidate position detection processing unit 222 by analyzing the macro observation image as well as which has been judged as an observation target by the detail judgment processing unit 223, can be identified as an estimated position, and thus, a position with a higher possibility of being identified as a position of a sample mass by the candidate position detection processing unit 222 analyzing the macro observation image, can be estimated in advance by the observation apparatus control unit 221 based on the observation history.

Alternatively, the observation apparatus control unit 221 can display, on the monitor 204a, magnified observation images of those with "Y" in the "magnified image pickup" column in the past n times of the observation histories so that a worker can select whether to be classified as a magnified observation candidate.

As a result, the position of a sample mass visually judged by the worker can be identified as an estimated position, and thus, a position with a higher possibility of being identified as a position of a sample mass by the candidate position detection processing unit 222 analyzing the macro observation image, can be estimated in advance by the observation apparatus control unit 221 based on the observation history.

Alternatively, if the detail judgment processing unit 223 is configured to output a judgment result on whether or not the cell mass is to be an observation target as a continuous value indicating a observation-target certainty factor, a cell mass having a certainty factor equal to or greater than a predetermined reference value can be classified as a magnified observation candidate, for example.

If a past observation history relating to the container C is not recorded in the observation history table 211, the observation apparatus control unit 221 may acquire coordinates selected at random from the macro observation images as an estimated position.

As a result, even if the observation of the container C is made for the first time and no observation history has been recorded, the candidate position detection processing unit 222 can acquire an estimated position of a sample mass in advance, and pickup an image of a magnified observation image during a period in which the candidate position detection processing unit 222 is identifying the position of the sample mass by analyzing the macro observation image.

Further, the observation apparatus control unit 221 may acquire a magnified observation candidate by combining the above.

Subsequently, the observation apparatus control unit 221 gives priority in photographing a magnified observation image for each of the magnified observation candidates extracted as above (S1050). The observation apparatus control unit 221 gives priority as follows, for example.

First, the observation apparatus control unit 221 gives the highest priority to a magnified observation candidate with "Y" in the "detail judgment" column in the past n times of the observation histories (where n is a natural number and, for example, which are the past n days if an observation interval is 1 day), for example.

As a result, pickup of a magnified observation image is carried out with higher priority being given to a sample mass judged as an observation target in the past by the detail judgment processing unit 223, and thus, pickup of a magnified observation image can be carried out in advance with respect to a sample mass with a high possibility of being extracted by the candidate position detection processing unit 222.

That is, the magnified observation candidate, which has been judged in the past to truly deserve a observation target by the detail judgment processing unit 223, can be expected to be detected as a magnified observation candidate by the candidate position detection processing unit 222 with an extremely high possibility, thereby being able to execute in advance more reliably pickup of a magnified observation image of magnified observation candidate detected by the candidate position detection processing unit 222 by giving priority as such.

If the detail judgment processing unit 223 is configured to output a judgment result on whether or not the sample mass is an observation target as a continuous value indicating observation-target certainty factor, it is preferable to give higher priority to a cell mass with a greater certainty factor. As a result, it becomes possible to execute pickup of a magnified observation image of a magnified observation candidate in advance more reliably.

Subsequently, the observation apparatus control unit 221 gives the next highest priority to a magnified observation candidate with "Y" in the "position detection" column, "Y" in the "magnified image pickup" column, and "N" in the "detail judgment" column, in the past n times of the observation histories, for example.

Even in the case of the magnified observation candidate having not been judged in the past to truly deserve a observation target by the detail judgment processing unit 223, if a magnified observation image has been picked up in the past, the high possibility of being detected as a magnified observation candidate by the candidate position detection processing unit 222 can be expected. Thus, by giving priority as such, it becomes possible to pick up, in advance more reliably, a magnified observation image of the magnified observation candidate detected by the candidate position detection processing unit 222.

Subsequently, the observation apparatus control unit 221 gives the next highest priority to a magnified observation candidate with "Y" in the "position detection" column, "N" in the "magnified image pickup" column, and "N" in the "detail judgment" column, in the past n times of the observation histories, for example.

Even in the case of a magnified observation image having not been picked up in the past, if it has been detected as a magnified observation candidate in the past by the candidate position detection processing unit 222, the high possibility of being detected, this time again, as a magnified observation candidate by the candidate position detection processing unit 222, is expected. Thus, by giving priority as such, it becomes possible to pick up, in advance more reliably, a magnified observation image of the magnified observation candidate detected by the candidate position detection processing unit 222.

Subsequently, the observation apparatus control unit 221 judges whether or not a list of coordinates of cell masses detected as magnified observation candidates has been notified by the candidate position detection processing unit 222 (S1060).

If the notice has not arrived yet at this point of time, the observation apparatus control unit 221 picks up magnified observation images of the magnified observation candidates, which have been acquired from the observation histories of the container C in the processing from S1030 to S1050, in order of priority (S1070 to S1090).

First, the observation apparatus control unit 221 judges whether or not the image pickup of the magnified observation images of all of the magnified observation candidates acquired from the observation histories has been finished (S1070).

If there is still a magnified observation candidate that has not been imaged yet, the observation apparatus control unit 221 sends an instruction to the micro observation unit 20 so as to cause the micro observation unit 20 to pickup a magnified observation image of the magnified observation candidate with the highest priority at that time (S1080).

Then, the observation apparatus control unit 221 records the magnified observation image obtained by image pickup in the storage unit 210 as an observation image 212, and records "Y" indicating that the magnified observation image has been picked up (indicating that image pickup has been finished) in the "magnified image pickup" column of the observation history table 211 together with the container ID, the date, the coordinate value of the cell mass in the observation history table 211 (S1090).

Returning to S1060, if the list of coordinates of the cell masses detected as the magnified observation candidates has been notified by the candidate position detection processing unit 222, the observation apparatus control unit 221 excludes, from the coordinates in this list, those corresponding to the coordinates of the magnified observation candidate estimated from the observation history as well as, those whose magnified observation images have already been picked up (S1110). As a result, duplication of pickup of the magnified observation images with respect to the same sample mass can be avoided.

Then, the observation apparatus control unit 221 sequentially performs image pickup of the magnified observation images of the aforementioned magnified observation candidates (S1110) and records "Y" indicating that the magnified observation image has been picked up in the "magnified image pickup" column of the observation history table 211 (S1120).

When image pickup of the magnified observation images of all the magnified observation candidates in the container C has been finished (S1130), the observation apparatus control unit 221 instructs the detail judgment processing unit 223 to judge whether or not these magnified observation candidates truly deserve observation targets (S1140).

Then, the detail judgment processing unit 223 judges whether or not the magnified observation candidate truly deserves a cell mass to be observed by analyzing the magnified observation image of each magnified observation candidate by template matching as described above (S3000).

Then, the detail judgment processing unit 223 records the judgment result in the "detail judgment" column of the observation history table 211 (S3010). The detail judgment processing unit 223 records "Y" in the "detail judgment" column of the observation history table 211, if having judged to be a cell mass that truly deserves an observation target. Whereas, if not having judged to be a cell mass that truly deserves an observation target, the detail judgment processing unit 223 records "N" in the "detail judgment" column of the observation history table 211.

When the aforementioned processing is finished with respect to one container C, the worker places the next container C on the conveying unit 30 and continues observation.

Second Embodiment

Figure 10:
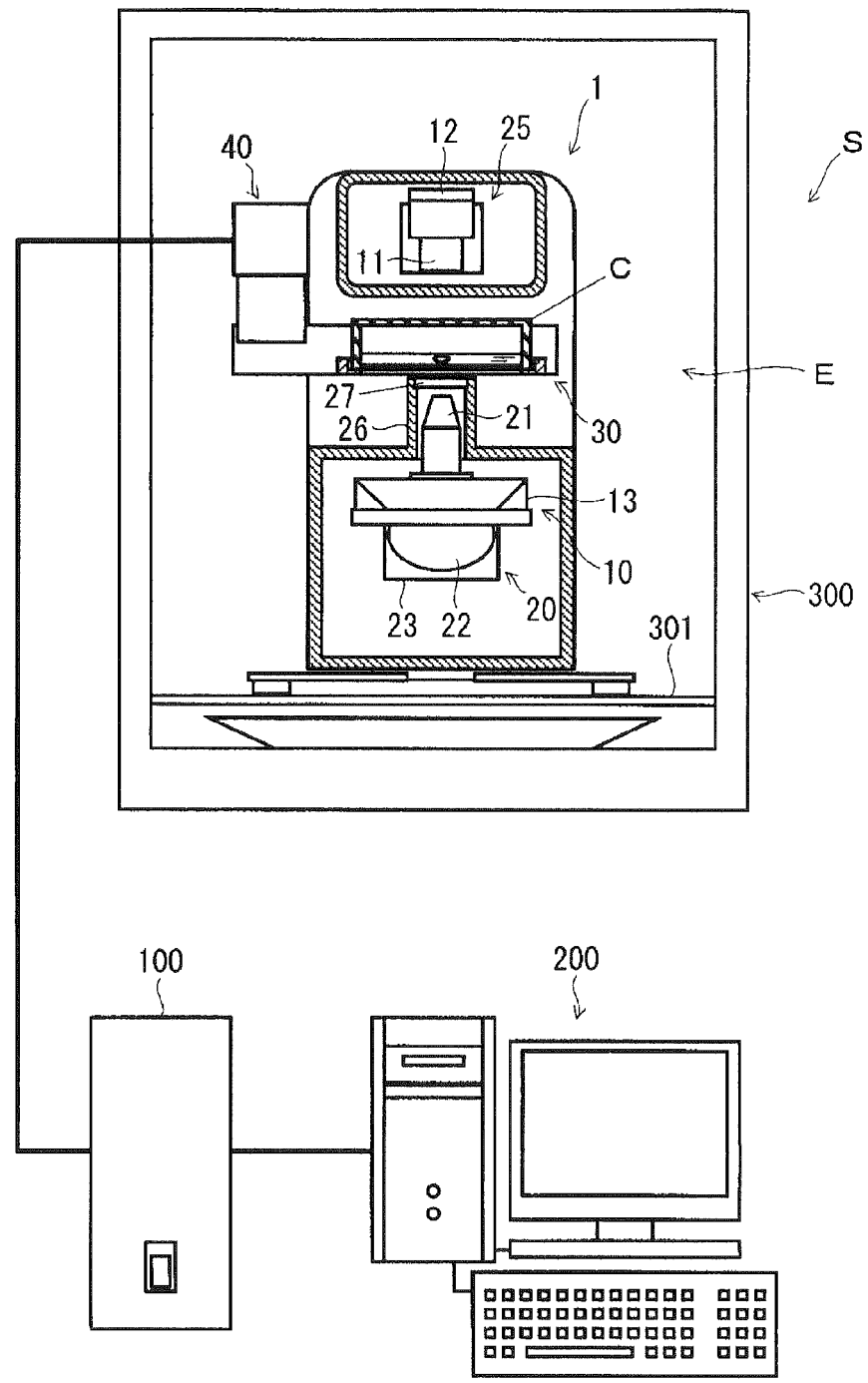
FIG. 10 is a configuration diagram of an observation apparatus system.

Next, a description will be given of a configuration of the observation system S according to a second embodiment of the present invention with reference to FIG. 10. FIG. 10 is a configuration diagram of the observation system S. Note that since a basic configuration of this embodiment is the same as that of the aforementioned first embodiment described with reference to FIGS. 1 to 9, the same reference numerals are given to the constituent elements common to those in the first embodiment, and the figures and the descriptions thereof will be omitted.

The observation apparatus 1 of the observation system S according to a second embodiment of the present invention is included in the interior of an incubator 300, as illustrated in FIG. 10. The incubator 300 is an example of a storage case for culturing or storing a cell, and forms a biologically and/or physically sealed storage space E. The observation apparatus 1 is installed on a shelf 301 provided in the interior of the incubator 300 and is used.

In many cases, the interior of the incubator 300 is kept in an interior environment such as a room temperature of 37° C. and a humidity of 100%. In such an environment, there is a high possibility of causing problems, such as image quality deterioration caused by fogging of an optical system occurring from the humidity; and short-circuits in electric components in a driving mechanism, a camera, and a lighting device. Thus, particularly in the case of arrangement in the interior of the incubator 300, a housing (main body 2) sealed in the observation apparatus 1 is required.

Even a configuration, in which the observation apparatus 1 is installed in the interior of the incubator 300 as such, can provide the observation apparatus 1 capable of identifying an emerging cell mass by observing the entire container C and further capable of magnifying the identified cell mass and observing the details thereof, in observing a cell being cultured in the container C. Further, the observation system S can be provided which is capable of continuously observing the cell mass identified as such from its emergence to completion of growth thereof.

Third Embodiment

Figure 11:
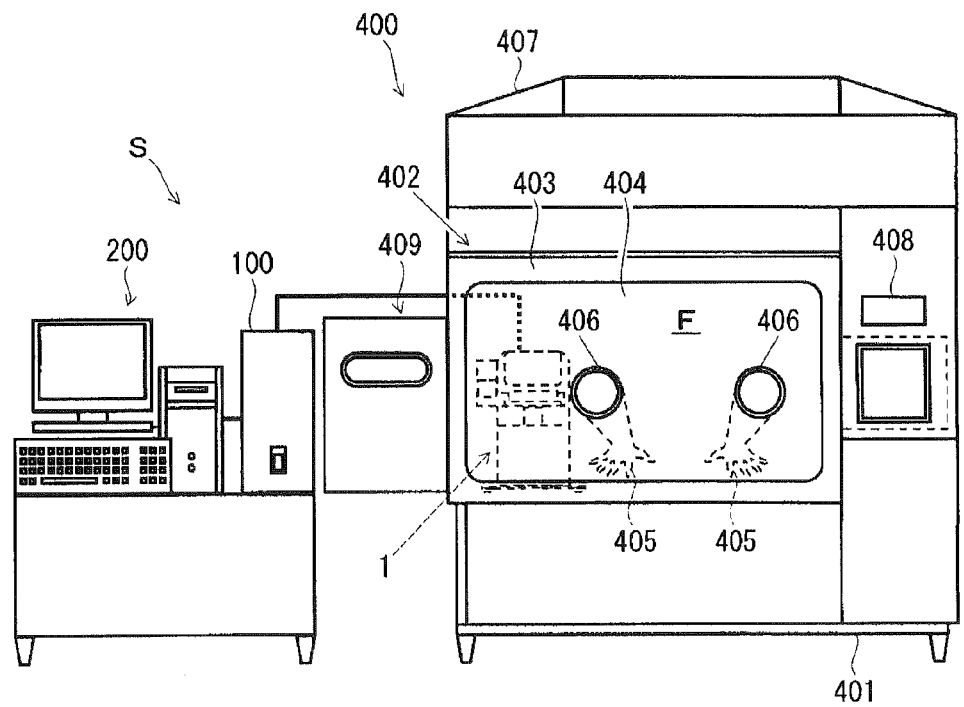
FIG. 11 is a configuration diagram of an observation apparatus system.
Figure 12:
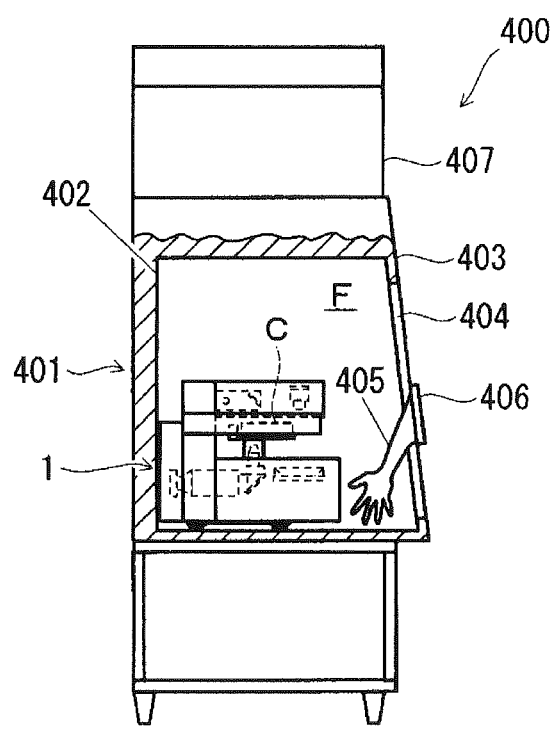
FIG. 12 is a partial sectional side view of an isolator.

Next, a description will be give of a configuration of the observation system. S according to a third embodiment of the present invention with reference to FIGS. 11 and 12. FIG. 11 is a configuration diagram of the observation systems, and FIG. 12 is a partial sectional side view of an isolator illustrated in FIG. 11. Note that since a basic configuration of this embodiment is the same as that of the aforementioned first embodiment described with reference to FIGS. 1 to 9, the same reference numerals are given to the constituent elements common to those in the first embodiment and the figure and the descriptions thereof will be omitted.

The observation apparatus 1 of the observation system S according to the third embodiment is housed in the interior of an isolator 400 as illustrated in FIGS. 11 and 12.

The isolator 400 includes a case 402 at the substantially center part of a main body 401. The case 402 forms a working space F sealed biologically and/or physically for executing a work relating to culture, treatment and observation of a cell. On the front side of the case 402, a front door 403 is provided so as to be capable of being opened/closed. The front door 403 is provided with a window portion 404 constituted by glass for viewing the interior of the working space F from the exterior thereof.

The window portion 404 of the front door 403 is provided with gloves 405 for conducting work in the working space F. The gloves 405 are provided in the form extending toward the working space F from the window portion 404 of the case 402. At locations at which the gloves 405 are attached to the window portion 404, opening portions 406 are provided. The worker inserts his/her hands into the gloves 405 from the opening portions 406 to wear them and conducts work in the working space F while watching the working space F in the sealed case 402 through the window portion 404. The two gloves 405 are provided in parallel in the lateral direction. Note that the numbers of the gloves 405 and their opening portions 406 are not limited to 2 but may be 3, 4 or more in some cases.

The isolator 400 further includes: a gas adjustment unit 407 on an upper part of the case 402; a main body operation unit 408 on the right side when the case 402 is seen from the front; and an incubator 409 on the left side.

As such, even the configuration, in which the observation apparatus 1 is installed in the interior of the isolator 400, can provide the observation apparatus 1 capable of identifying an emerging cell mass by observing the entire container C and further capable of magnifying the identified cell mass and observing the details thereof, in observing a cell being cultured in the container C. Further, the observation system S can be provided which is capable of continuously observing the cell mass identified as such from its emergence to completion of growth thereof. Note that the observation apparatus 1 may be installed in the interior of the incubator 409.

Fourth Embodiment

Figure 13:
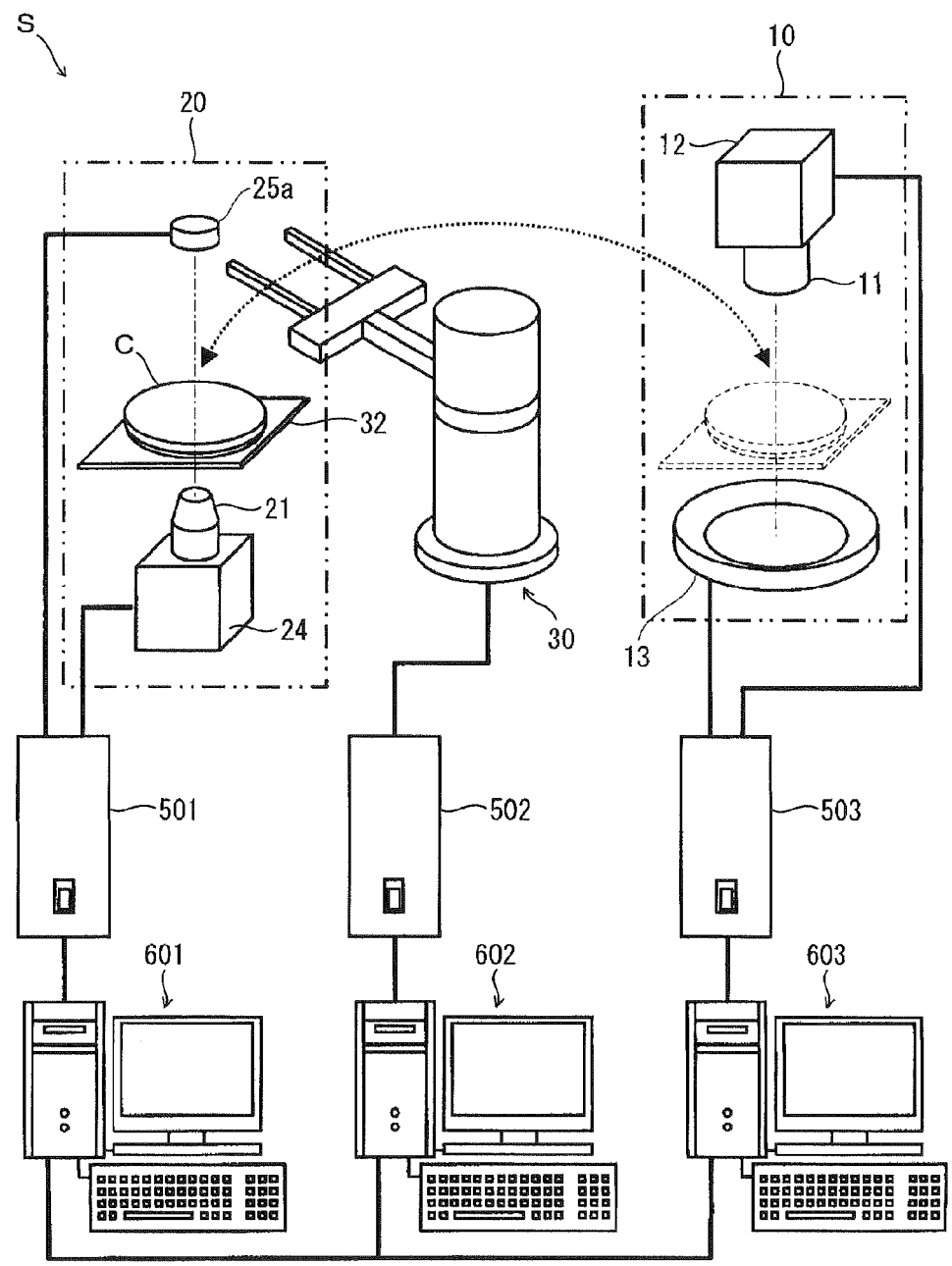
FIG. 13 is a configuration diagram of an observation apparatus system.

Next, a description will be given of a configuration of the observation system S according to a fourth embodiment of the present invention with reference to FIG. 13. FIG. 13 is a configuration diagram of the observation system S. Note that since a basic configuration of this embodiment is the same as that of the aforementioned first embodiment described with reference to FIGS. 1 to 9, the same reference numerals are given to the constituent elements common to those in the first embodiment and the figure and the descriptions thereof will be omitted.

The observation system S according to the fourth embodiment includes the macro observation unit 10, the micro observation unit 20, and the conveying unit 30 as illustrated in FIG. 13, and they are provided independently from one another.

For the macro observation unit 10, the micro observation unit 20, and the conveying unit 30, provided are control devices 501 to 503, which are configured to respectively individually control them, and computers 601 to 603, which are configured to respectively individually send instructions to them. The three computers 601 to 603 are connected to one another with network cables so that they can communicate with one another, thereby being able to perform the macro observation, micro observation, and conveyance of the container C in coordination with one another.

Note that a configuration may be such that another computer configured to integrally coordinate the three computers is provided. Further, a configuration may be such that a single computer may be provided and instructions are sent from this single computer to the control devices 501 to 503. Furthermore, a configuration may be such that a single computer and a single control device may be provided and the macro observation unit, the micro observation unit, and the conveying unit are controlled from the single computer and the single control device.

Further, the conveying unit 30 illustrated in FIG. 13 configured to convey the container C between the macro observation unit 10 and the micro observation unit 20 by moving rotationally, however, similarly to the first embodiment, the conveying unit 30 may be configured to convey the container C by moving horizontally. The container C is placed on a placement tray 32 which is commonly used for the macro observation unit 10 and the micro observation unit 20. Positioning of the placement tray 32 is performed with respect to the macro observation unit 10 and the micro observation unit 20, and positioning of the container C is performed with respect to the placement tray 32.

Even a configuration, in which the macro observation unit 10, the micro observation unit 20, and the conveying unit 30 are independently individually controlled as such, can provide the observation system S capable of identifying an emerging cell mass by observing the entire container C and further capable of magnifying the identified cell mass and observing the details thereof, in observing a cell being cultured in the container C. Further, the observation system S can be provided which is capable of continuously observing the cell mass identified as such from its emergence to completion of growth thereof.

In a small working space such as an incubator or an isolator, by configuring the macro observation unit, the micro observation unit, and the conveying unit as separate mechanisms, flexible configuration in arrangement of units are enabled, thereby being able to effectively use the working space.

Embodiments of the present invention has been described, and according to an embodiment of the present invention, the observation apparatus control unit 221 acquires an estimated position of a cell mass in the container C based on the past observation history recorded in the observation history table 211, sends this estimated position to the micro observation unit of the observation apparatus 1, and causes the micro observation unit 20 to pick up a magnified observation image of the vicinity of the estimated position, that is, a part of an area in the container C including this estimated position, while waiting for the identification result of the position of each cell mass in the container C to be sent from the candidate position detection processing unit 222.

As a result, the observation apparatus control unit 221 can proceed with image pickup of a magnified observation image without wasting a waiting time while a magnified observation candidate is being detected by the candidate position detection processing unit 222, thereby being able to improve the efficiency of a work of detecting a sample mass, which deserves an observation target, from the container C and magnifying and picking up an image of a part of the sample mass.

Further, the observation apparatus control unit 221 does not perform image pickup of the vicinity of the position if an image of the vicinity of the position, that is, a part of an area in the container C including this position has already been picked up based on the estimated position, when the position of the sample mass is identified by the candidate position detection processing unit 222.

As a result, since it is possible not to perform image pickup in a duplicate manner for an area for which a magnified observation image has been picked up in advance based on the estimated position, thereby being able to reduce the time required for observing one container C (time required for picking up a macro observation image, detecting magnified observation candidates, picking up a magnified observation image for each magnified observation candidate, and performing detail judgment of each magnified observation candidate).

Further, the observation apparatus control unit 221 assigns priorities to estimated positions by a predetermined method, and picks up a magnified observation image of each estimated position in order of priority. This priority is calculated such that the higher the priority of the position is, the more reliably the position is detected as a magnified observation candidate by the candidate position detection processing unit 222.

As a result, the observation apparatus control unit 221 can get done with pickup of magnified observation images of more magnified observation candidates in this list in a time period until when a list of coordinates of the magnified observation candidates has been obtained from the candidate position detection processing unit 222.

The above embodiments of the present invention are simply for facilitating the understanding of the present invention and are not in any way to be construed as limiting the present invention. The present invention may variously be changed or altered without departing from its spirit and encompass equivalents thereof.

For example, aforementioned embodiments have been described in which a single culture container is observed, however, a plurality of containers may be observed at the same time by using a tray on which a plurality of culture containers can be placed.

Further, in aforementioned embodiments, the CMOS camera 12 is used for the image pickup unit of the macro observation unit 10 and the CCD camera 24 for the image pickup unit of the micro observation unit 20, but a type of cameras to be used may be either of the CMOS camera and the CCD camera.

What is claimed is:

1. An observation system configured to observe a sample mass formed of samples gathering in a container containing the samples and a solution, the observation system comprising:

an entire image pickup unit configured to pick up an image of the entire container;

a sample mass identification unit configured to identify a sample mass formed in the container, from a macro observation image obtained by picking up an image of the entire container;

a magnifying image pickup unit configured to magnify and pick up an image of a part of an area in the container including the sample mass identified by the sample mass identification unit; and a history information storage unit configured to store position information of the sample mass in association with time and date information, the magnifying image pickup unit further configured to magnify and pick up an image of a part of an area in the container based on the past position information stored in the history information storage unit, while the sample mass identification unit is executing processing of identifying the sample mass.

2. The observation system according to claim 1, wherein when the sample mass is identified by the sample mass identifying unit and when an image of an area including the sample mass has already been picked up, the magnifying image pickup unit does not pick up an image of the area.

3. The observation system according to claim 1, wherein while the sample mass identification unit is executing processing of identifying the sample mass, in a case where a predetermined number or more of pieces of the position information estimated to be position information of the same sample mass are stored in the history information storage unit, the magnifying image pickup unit acquires an estimated position of a sample mass in the container based on the position information, and magnifies and picks up an image of a part of an area in the container including the estimated position.

4. The observation system according to claim 3, wherein in a case where a difference between first position information and second position information stored in the history information storage unit is within a predetermined range, the magnifying image pickup unit estimates that the first position information and the second position information are position information of the same sample mass.

5. The observation system according to claim 1, further comprising:

a detail judgment unit configured to
 extract a predetermined feature amount from a magnified observation image obtained by magnifying and picking up, with the magnifying image pickup unit, an image of a part of an area in the container including a sample mass identified by the sample mass identification unit,
 judge whether the sample mass whose magnified observation image has been picked up is to be an observation target or not, based on the predetermined feature amount, and
 store a judgment result in the history information storage unit, in association with position information of the sample mass, wherein while the sample mass identification unit is executing processing of identifying a sample mass in the container, the magnifying image pickup unit acquires an estimated position of the sample mass in the container, based on the position information of the sample mass judged to be the observation target among the past position information stored in the history information storage unit, and magnifies and picks up an image of a part of an area in the container including the estimated position.

6. The observation system according to claim 1, further comprising:

an observation apparatus control unit configured to, when the magnifying image pickup unit has magnified and picked up an image of a part of an area in the container including the sample mass identified by the sample mass identification unit, store information indicative that an image of the sample mass has been picked up in the history information storage unit, in association with position information of the sample mass, wherein while the sample mass identification unit is executing processing of identifying a sample mass in the container, the magnifying image pickup unit acquires an estimated position of the sample mass in the container, based on the position information associated with the information indicative that an image of the sample mass has been picked up among the past position information stored in the history information storage unit, and magnifies and picks up an image of a part of an area in the container including the estimated position.

7. The observation system according to claim 1, further comprising:

an observation apparatus control unit configured to, when the magnifying image pickup unit has magnified and picked up an image of a part of an area in the container including the sample mass identified by the sample mass identification unit, store information indicative that an image of the sample mass has been picked up in the history information storage unit, in association with position information of the sample mass, wherein while the sample mass identification unit is executing processing of identifying a sample mass in the container, the magnifying image pickup unit acquires an estimated position of the sample mass in the container, based on the position information not associated with the information indicative that an image of the sample mass has been picked up among the past position information stored in the history information storage unit, and magnifies and picks up an image of a part of an area in the container including the estimated position.

8. The observation system according to claim 1, further comprising:

an observation apparatus control unit configured to, when the magnifying image pickup unit has magnified and picked up an image of a part of an area in the container including the sample mass identified by the sample mass identification unit, store information indicative that an image of the sample mass has been picked up in the history information storage unit, in association with position information of the sample mass; and a detail judgment unit configured to
 extract a predetermined feature amount from a magnified observation image obtained by magnifying and picking up an image of the part of the area with the magnifying image pickup unit,
 judge whether the sample mass whose magnified observation image has been picked up is to be an observation target or not, based on the extracted predetermined feature amount, and
 store a judgment result in the history information storage unit, in association with position information of the sample mass, wherein while the sample mass identification unit is executing processing of identifying a sample mass in the container, the magnifying image pickup unit
 acquires a first estimated position of the sample mass in the container, based on position information associated with a judgment result that the sample mass is the observation target among a plurality of pieces of the past position information stored in the history information storage unit, and magnifies and picks up an image of an area in the container including the first estimated position, and thereafter,
 acquires a second estimated position of the sample mass in the container, based on position information associated with the information indicative that an image of the sample mass has been picked up among the plurality of pieces of the position information, and magnifies and picks up an image of an area in the container including the second estimated position, and thereafter, acquires a third estimated position of the sample mass in the container, based on position information not associated with the information indicative that an image of the sample mass has been picked up among the plurality of pieces of the position information, and magnifies and picks up an image of an area in the container including the third estimated position.

9. The observation system according to claim 1, wherein the sample contained in the container is a cell, and the solution is a culture fluid for the cell.

10. A computer readable recording medium having a program recorded therein, the program causing a computer, configured to control an observation system configured to observe a sample mass formed of samples gathering in a container containing the samples and a solution, to execute steps of:

picking up an image of the entire container;

identifying a sample mass formed in the container from a macro observation image obtained by picking up an image of the entire container;

magnifying and picking up an image of a part of an area in the container including the identified sample mass;

storing position information of the sample mass in a history information storage unit, in association with time and date information; and magnifying and picking up an image of a part of an area in the container based on the past position information stored in the history information storage unit while executing processing of identifying the sample mass.

11. A method for controlling an observation system configured to observe a sample mass formed of samples gathering in a container containing the samples and a solution, the method comprising:

picking up an image of the entire container, with the observation system;

identifying, with the observation system, a sample mass formed in the container from a macro observation image obtained by picking up an image of the entire container;

magnifying and picking up, with the observation system, an image of a part of an area in the container including the identified sample mass;

storing, with the observation system, position information of the sample mass in a history information storage unit, in association with time and date information; and magnifying and picking up, with the observation system, an image of a part of an area in the container based on the past position information stored in the history information storage unit, while executing processing of identifying the sample mass.

* * * * *